US006884392B2

(12) United States Patent
Malkin et al.

(10) Patent No.: US 6,884,392 B2
(45) Date of Patent: Apr. 26, 2005

(54) APPARATUS AND METHOD FOR STEAM REPROCESSING FLEXIBLE ENDOSCOPES

(75) Inventors: Roy K. Malkin, Lakeville, MN (US); Roland C. Kippenhan, Jr., Woodbury, MN (US); Michael P. Petersen, Eden Prairie, MN (US); Thomas L. Fenton, St. Louis Park, MN (US)

(73) Assignee: Minntech Corporation, Minneapolis, MN (US)

( * ) Notice: Subject to any disclaimer, the term of this patent is extended or adjusted under 35 U.S.C. 154(b) by 41 days.

(21) Appl. No.: 10/292,747

(22) Filed: Nov. 12, 2002

(65) Prior Publication Data

US 2004/0091389 A1 May 13, 2004

(51) Int. Cl.[7] .................................................. A61L 2/08
(52) U.S. Cl. ......................... 422/26; 134/198; 206/363; 206/438; 422/1; 422/292; 422/297; 422/300
(58) Field of Search .............................. 422/26, 1, 292, 422/297, 300; 134/198; 206/363, 438

(56) References Cited

U.S. PATENT DOCUMENTS

| | | | |
|---|---|---|---|
| 4,592,896 A | * | 6/1986 | Runnells et al. ............. 422/109 |
| 5,091,343 A | | 2/1992 | Schneider et al. |
| 5,225,160 A | * | 7/1993 | Sanford et al. ................ 422/28 |
| 5,279,799 A | * | 1/1994 | Moser ......................... 422/292 |
| 5,575,756 A | | 11/1996 | Karasawa et al. |
| 5,609,561 A | | 3/1997 | Uehara et al. |
| 5,871,441 A | | 2/1999 | Ishiguro et al. |
| 6,030,339 A | | 2/2000 | Tatsuno et al. |
| 6,068,815 A | * | 5/2000 | Oberleitner et al. ........... 422/28 |
| 6,234,310 B1 | | 5/2001 | Goldhaber |
| 6,286,527 B1 | | 9/2001 | Stanley |
| 6,416,525 B1 | | 7/2002 | Shibata |
| 6,514,198 B1 | | 2/2003 | Ishibiki |
| 6,555,054 B1 | * | 4/2003 | Kral et al. ..................... 422/28 |
| 6,558,620 B1 | * | 5/2003 | Sanford et al. ................ 422/28 |
| 2002/0001551 A1 | | 1/2002 | Moriyama |
| 2002/0015673 A1 | | 2/2002 | Moriyama |
| 2002/0016525 A1 | | 2/2002 | Ishibiki |
| 2002/0072654 A1 | | 6/2002 | Takase |
| 2004/0197248 A1 | | 10/2004 | Hasegawa et al. |

FOREIGN PATENT DOCUMENTS

| | | |
|---|---|---|
| JP | 3226328 B | 12/1993 |
| JP | 2002-306412 | 10/2002 |
| JP | 2002-325719 | 12/2002 |

OTHER PUBLICATIONS

International Search Report, PCT, Jun. 30, 2004, 3 pages.

* cited by examiner

*Primary Examiner*—Krisanne Jastrzab

(57) ABSTRACT

A system for reprocessing flexible endoscopes having lumen therein. The reprocessing system deploys steam to disinfect and/or sterilize the endoscopes, and designs, components, and methods for reducing or balancing the reprocessing cycle time and the effects of thermal expansion and contraction on the endoscopes.

68 Claims, 12 Drawing Sheets ated with a conventional steam autoclave. Steam autoclaves have also been modified to operate under low pressure cycling programs to increase the rate of steam penetration into the medical devices or associated packages of medical devices undergoing sterilization. Steam sterilization using gravity, high pressure or pre-vacuum create an environment where rapid changes in temperature can take place. In particular, highly complex instruments which are often formed and assembled with very precise dimensions, close assembly tolerances, and sensitive optical components, such as endoscopes, may be destroyed or have their useful lives severely curtailed by harsh sterilization methods employing high temperatures and high or low pressures.

APPARATUS AND METHOD FOR STEAM REPROCESSING FLEXIBLE ENDOSCOPES

TECHNICAL FIELD

The present invention relates to apparatus, articles, methods, and systems for cleaning, disinfecting, and/or sterilizing (i.e., reprocessing) medical devices, such as flexible endoscopes, including the use of steam.

BACKGROUND

Sterilization connotes the absence of all life forms, including bacterial endospores that are the living organisms most resistant to conventional sterilants. Disinfection, by distinction, only connotes the absence of pathogenic life forms (i.e., a bacterial endospore is not itself a pathogenic life form, but can produce such pathogens). Microbial decontamination is generic to both sterilization and disinfection.

Robust medical equipment is often sterilized at high temperatures. Commonly, the equipment is sterilized in a steam autoclave under a combination of high temperature and pressure. While such sterilization methods are very effective for more durable medical instruments, advanced medical instruments formed of rubber and plastic components with adhesives are delicate and wholly unsuited to the high temperatures and pressures associated with a conventional steam autoclave. Steam autoclaves have also been modified to operate under low pressure cycling programs to increase the rate of steam penetration into the medical devices or associated packages of medical devices undergoing sterilization. Steam sterilization using gravity, high pressure or pre-vacuum create an environment where rapid changes in temperature can take place. In particular, highly complex instruments which are often formed and assembled with very precise dimensions, close assembly tolerances, and sensitive optical components, such as endoscopes, may be destroyed or have their useful lives severely curtailed by harsh sterilization methods employing high temperatures and high or low pressures.

Further, endoscopes in particular present problems in that such devices typically have numerous exterior crevices and interior lumens which can harbor microbes and thus be difficult to clean and sterilize using ordinary techniques. The employment of a fast-acting yet gentle sterilization method is desirable for reprocessing sensitive instruments such as endoscopes. Other medical or dental instruments which comprise lumens are also in need of methods of cleaning and sterilizing which employ an effective reprocessing system which will not harm sensitive components and materials. Further, the need exists for a reprocessing system having a shorter reprocessing cycle time.

Early efforts to sterilize sensitive medical instruments, such as endoscopes, have met with limited success, and all conventional methods have associated problems or detractions. Sensitive medical instruments, such as endoscopes, are often sterilized by exposure to ethylene oxide which is thermally less severe than steam. The endoscope must be exposed to ethylene oxide-containing gas for a relatively long period, on the order of three to four hours. Thereafter, eight to twelve hours are normally required for de-gassing or desorbing ethylene oxide from plastic and other materials which are capable of absorbing the ethylene oxide. The pressurization and depressurization cycles of ethylene oxide sterilization may damage lens systems and other delicate instruments which are commonly integral with endoscopes.

Moreover, the ethylene oxide is relatively expensive. It is sufficiently toxic and volatile that extensive precautions are commonly taken to assure operator safety. Other possible gaseous chemical sterilants include methyl bromide gas, beta-propiolactone gas, and ozone gas.

Liquid systems are commonly used for disinfecting endoscopes and other heat sensitive and delicate instruments. Use of liquid sterilants or disinfectants to achieve disinfection is normally rapid, cost-effective and does minimal damage to the medical devices. Current liquid chemical sterilants include glutaraldehyde solution, ortho-phthalaldehyde solution, formaldehyde solution, hydrogen peroxide solution, hydrogen peroxide/peracetic acid solution, and peracetic acid solution.

Commonly, a technician mixes a sterilant composition and manually immerses the item to be disinfected. Alternatively, a premixed sterilant composition can be used into which the item to be disinfected can be immersed. The immersion is timed by the technician. Technician variation in the mixing, timing and equipment handling raises problems of assurance and reproducibility of the manual disinfection process. Rinsing of the items to remove chemical residues also adds a variable that reduces the assurance of disinfection or sterility. Once rinsed, the disinfected endoscope or other item is susceptible to recontamination by airborne microbes.

Conventional liquid systems require complete immersion of the endoscope in the liquid solution. Large and bulky items such as endoscopes require large immersion containers and equally large volumes of expensive sterilant or disinfecting solution. Further, merely soaking endoscopes in a sterilant or disinfectant is less preferred since numerous pockets exist within the tubing that the sterilant or detergent cannot reach effectively. This leaves areas of potential contamination within the endoscope.

With the prevalence of highly contagious diseases such as Hepatitis B and Acquired Immune Deficiency Syndrome, effective sterilization, or disposal, of all medical tools becomes mandatory. Accordingly, an ineffective effort to sterilize endoscopes by merely soaking is unacceptable. For example, U.S. Pat. No. 5,091,343 discloses a liquid sterilization system which involves placing the instrument to be sterilized in a tray or cassette which is then covered and positioned within a liquid sterilization unit. Within the unit the cassette or tray is filled with liquid sterilant, rinsed with a sterile rinse water and the rinse water drained away. As the rinse water is drained away, sterile air is introduced into the cassette or tray. The cassette or tray is removed from the unit and the process is completed with uncovering the instrument and removing it for storage or use. A major drawback of this type of process is the lack of assurance of a sufficient flow of sterilant and rinse water through the interior passages of the instrument. The low pressure circulation of the liquid sterilant in the cassette or tray and the numerous pockets inherent in such a tubular instrument provides no assurance that adequate sterilization is attained in the interior passages of the instrument. The exterior surfaces of instruments, such as endoscopes, typically have multiple connectors and branches which can define small crevices or niches harboring microbes. Because of this, low pressure circulation liquid sterilization systems, which rely on complete submersion of the endoscope, may also be inadequate to assure complete sterilization of all exterior surfaces.

An improved approach is reported in U.S. Pat. No. 6,068,815 to Oberleitner, et al. Oberleitner reports a reprocessing system by which chemical sterilant is introduced to a lumen of an endoscope by pneumatic force.

Steam sterilization is widely considered to be the best available sterilization technique. A need exists to provide a device which can be used in combination with a fast-acting sterilization method to effectively reprocess and sterilize complex medical instruments having channels or lumens, in particular, such as endoscopes. Preferably, the device would be capable of combining all necessary reprocessing steps into a single system that can carry out the reprocessing of a device without or with reduced human intervention and without or with reduced harm to the medical device.

SUMMARY OF THE INVENTION

One embodiment of the present invention is an apparatus for reprocessing an endoscope having an external surface and a lumen. This embodiment includes an enclosure having a reprocessing bay therein for receiving the endoscope and a steam source in fluid communication with the reprocessing bay. A fluid sprayer is in fluid communication with the steam source for spraying steam onto the external surface of the endoscope. A fluid conduit is in fluid communication with the steam source and configured to allow steam from the steam source to flow through the fluid conduit into the lumen of the endoscope.

Another embodiment of the present invention includes a method for reprocessing a flexible endoscope, which includes placing the endoscope into a steam reprocessing bay of a reprocessing apparatus. The endoscope has an exterior surface and lumen. This embodiment further includes applying steam to the exterior surface of the endoscope and flowing steam through the lumen of the endoscope. Further, this embodiment includes controlling a dimensional change to the endoscope during the reprocessing method.

Another embodiment of the present invention includes an endoscope assembly for use with a endoscope reprocessing apparatus. This embodiment includes an endoscope having lumen therein. A frame is included on which the endoscope may be positioned during reprocessing within a reprocessing apparatus. The frame includes an assembly connector connectable to the lumen such that reprocessing fluid from the reprocessing can flow into the lumen. A reprocessor connector is positioned and configured to connect to a reprocessing connector of the reprocessing apparatus due to insertion of the frame into the reprocessing apparatus.

Still another embodiment of the present invention includes a method for reprocessing the endoscope following an endoscopic procedure that involves placing the endoscope into a steam reprocessing bay of a reprocessing apparatus. The endoscope has an exterior surface and lumen. This embodiment further involves applying steam to the exterior surface of the endoscope and flowing flow of steam through the lumen of the endoscope. Further, this embodiment includes controlling the temperature the endoscope during the reprocessing method. This embodiment can be used with respect to endoscope that was previously used in an endoscopic procedure or one that has never been used.

The present invention further includes a significant number of variations of the above described embodiments.

DETAILED DESCRIPTION OF PREFERRED EMBODIMENTS

The present invention provides an apparatus, componentry, methodology, and an integrated system for processing or reprocessing medical devices with minimal human intervention to yield a clean, disinfected, decontaminated, or sterilized device. The term "reprocessing" is intended to encompass cleaning, disinfecting, decontaminating, and/or terminally sterilizing medical devices, instruments or apparatus used in an earlier procedure, such as an endoscopic procedure. "Reprocessing" also covers the same or similar steps carried out on new or never-used devices, instruments, or apparatuses, whether these items are intended for one-time or repeated use. The embodiments described below include (or can include) but are not limited to the use of one or more of a liquid for rinsing an endoscope E (or other medical or non-medical device), a liquid for heat-up, a gas for heat-up, a liquid detergent solution for washing, a liquid sterilant, a steam sterilant, a steam-gas mixture sterilant, a liquid for cool-down, and a gas for cool-down. In other words, one embodiment can, for example, involve only the use of a warm water detergent solution for washing, warmer water for rinsing, a high temperature steam for sterilizing, and a lower temperature steam for cool-down. Alternatively, the high temperature steam can be replaced with the lower temperature steam and formaldehyde mixture used more prevalently in European reprocessing systems.

Figure 1:
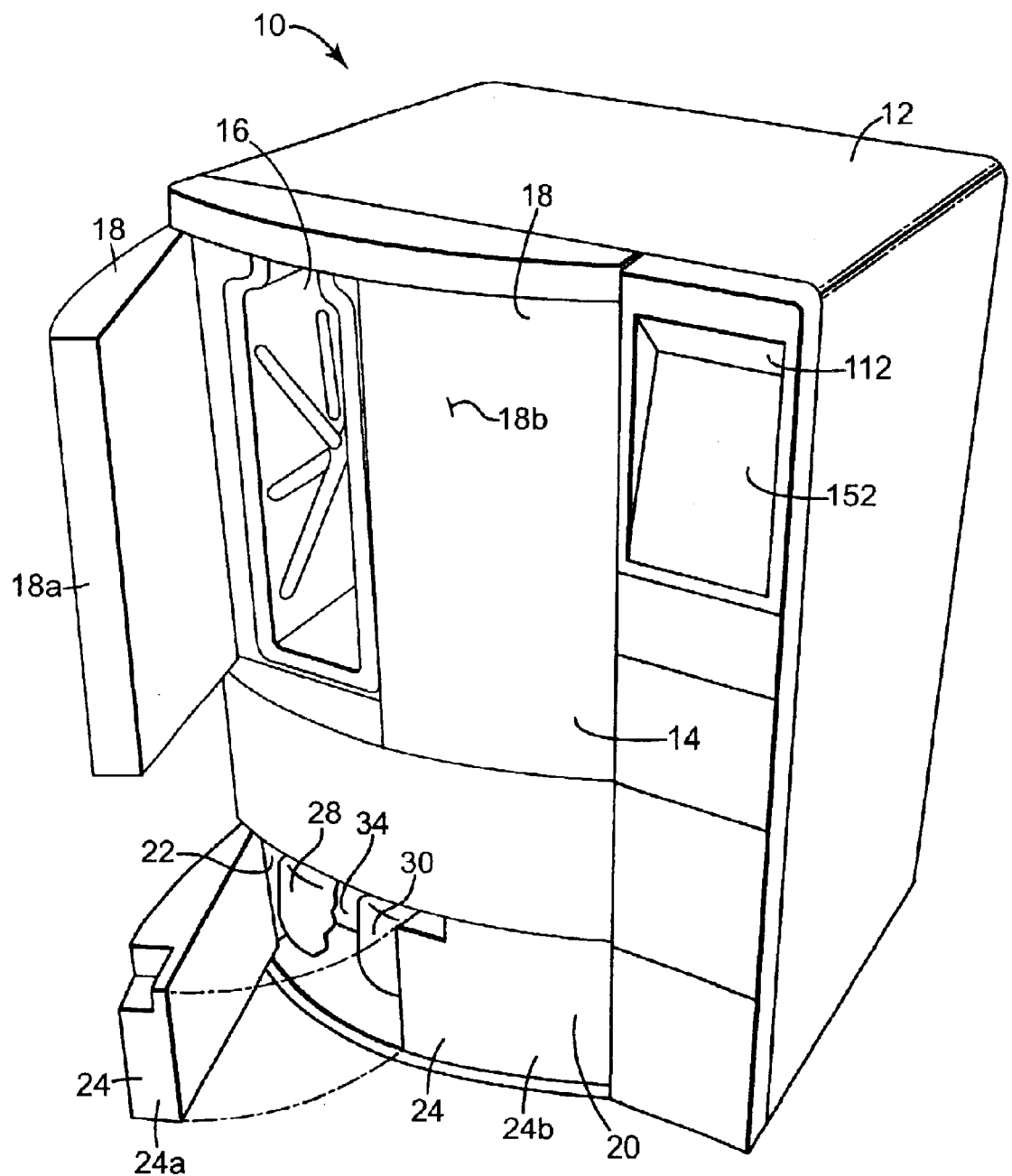
FIG. 1 is an exterior perspective view of an embodiment of the present invention.

The embodiment of the present invention shown in FIG. 1 is intended to provide an improved system, componentry, and methodology for cleaning, disinfecting, and/or terminally sterilizing flexible endoscopic devices. It is, however, well within the conception of the invention to adapt the invention to also clean, disinfect, and/or sterilize a variety of medical instruments, including but not limited to other types of medical instruments having a lumen, such as, for example, catheters, or medical instrumentation sensitive to thermal shock.

Referring now to FIGS. 1–5, an endoscope reprocessing system according to the principles of the present invention is shown and generally indicated at 10. An exterior housing 12 or enclosure can be provided to arrange, contain and provide protection for the components of the reprocessing apparatus or system 10. A reprocessing bay cabinet 14 of the housing 12 can be configured to contain at least one reprocessing bay 16 (or chamber). The reprocessing bay cabinet 14 can be equipped with at least one cabinet access door 18. The preferred embodiment shown in FIGS. 1–2 can be configured to have one reprocessing bay 16, although the concept of the present invention is not limited to one reprocessing bay 16.

Figure 9:
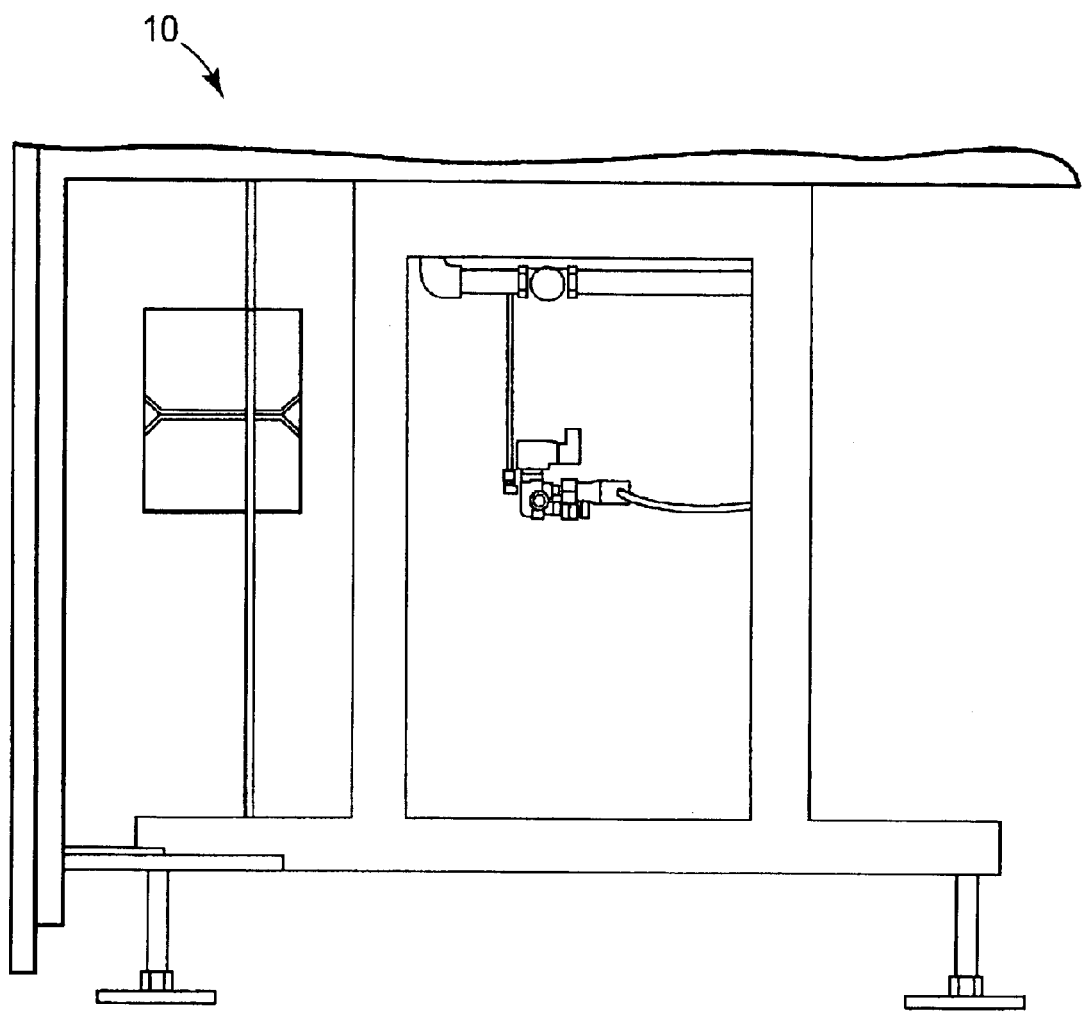
FIG. 9 is a side view of a lower portion or variation of the embodiment shown in FIG. 7, including fluid conduit and valving.
Figure 10:
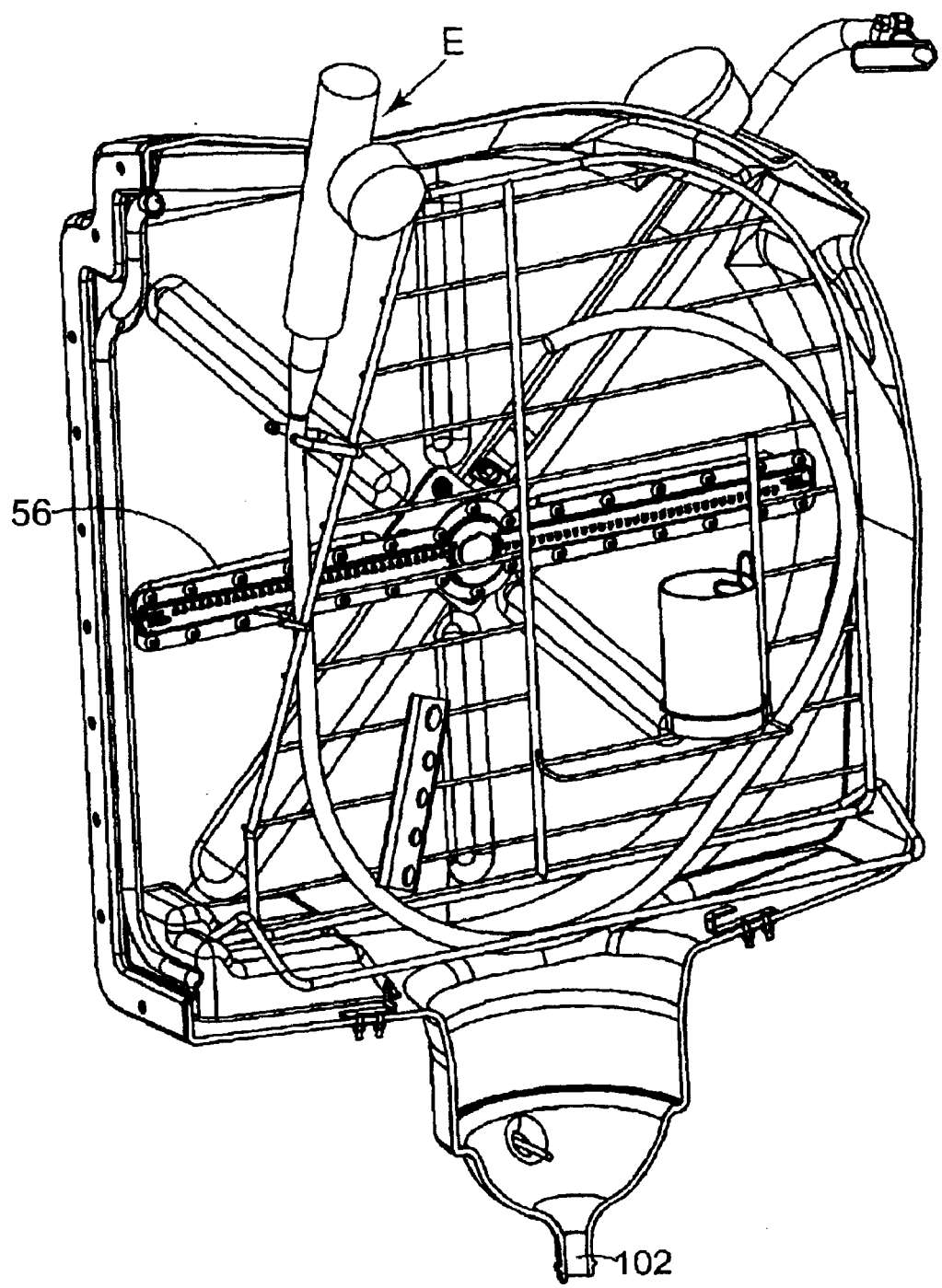
FIG. 10 a cut-away perspective view of a reprocessing bay within the embodiment shown in FIG. 7.

A drawer 20, which can be configured to contain support components, generally indicated at 22, can be equipped with at least one drawer access door 24. The embodiment shown in FIG. 1 can be configured to have two drawer access doors 24a, 24b, which are shown with one drawer access door 24a in the open position allowing access to the support components 22 and another drawer access door 24b in the closed position. The support components 22, contained within the drawer 20 or elsewhere in the system 10, can include all or some number of the following: a detergent container 26, one or more chemical sterilant component containers 28, 30, a water heater 32, a hot water tank 34, an optional reaction chamber 36, a load sensor 38, an electric motor and pump 40, an air compressor 42, a compressed air tank 44, a steam source or generator 46 (e.g., house steam as indicated in FIG. 9 or another source independent of system 10, or an onboard source such a boiler, pressure chamber, hot plate, or other steam means), and a vacuum source (e.g., vacuum pump, house vacuum system; not shown). Other components can include, for example, duplicates of the above components (e.g., additional steam generators or sources), temperature sensors (e.g., thermometers, thermocouples, and other means for sensing temperature), electronic, pneumatic, or hydraulic valves and other actuators, fluid conduits, fluid manifolds, fluid connectors, flow meters, mixing valves, pressure sensors, sterile barrier packaging, displays, touchscreen, keypads, other sources of steam, and all manner of electronic systems to program, monitor and control (e.g., programmably control) sterilizer/reprocessor function or actions and carry out critical or non-critical diagnostic functions or actions such as endoscope channel blockage testing, endoscope channel integrity (also referred to as leak testing) and endoscope flow testing.

As used herein, the term "chemical sterilant component" refers to a precursor composition that is mixed, reacted, or diluted with another substance to provide a chemical sterilant. The term "chemical sterilant component" is also intended to cover chemical sterilants that do not require reaction or dilution. The embodiment shown in FIG. 2 can be configured with two chemical sterilant component containers 28, 30 which can serve to contain two components of a multi-component concentrate system. It is, however, within the concept of the present invention to configure the reprocessing system to include a greater or lesser number of chemical sterilant component containers, or no containers, depending upon the number of components required for the sterilant used. The use of a chemical sterilant is optional in the methods of the present invention, and the inclusion of chemical sterilant component containers such as 28 and 30 in the reprocessing system 10 is likewise optional. When no chemical sterilant is used, or where a ready-to-use sterilant is employed, reaction chamber 36 is not necessary.

One version of the preferred embodiment may not involve the use of a chemical sterilant, but deploy steam as the sterilant. Steam sterilization, which will be described in greater detail later herein, can be achieved for example using higher temperature steam or low temperature steam mixed with formaldehyde or other sterilizing gases. Another version of the preferred embodiment may involve the use of both chemical and steam sterilants. A variety of combinations is contemplated as part of the present invention.

If the reprocessing system 10 includes two or more reprocessing bays 16, the reprocessing system could be configured so that each reprocessing bay can be operated or cycled independently and asynchronously. To support such independent operation, the reprocessing system 10 may be equipped with an independently operated electric motor and pump 40, one for each reprocessing bay.

Figure 5:
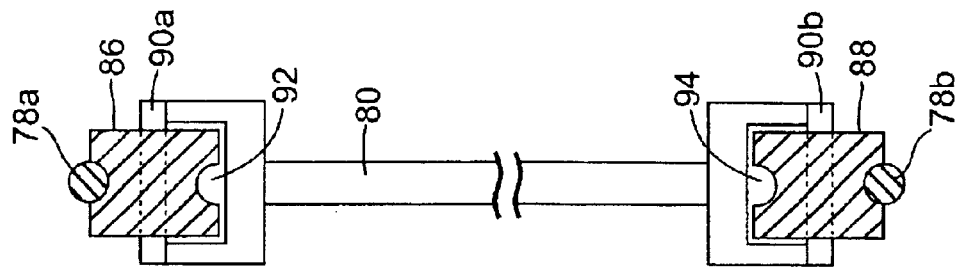
FIG. 5 is a perspective view of a cassette or support frame, which may be used with the embodiments shown in FIGS. 1–4.
Figure 6:
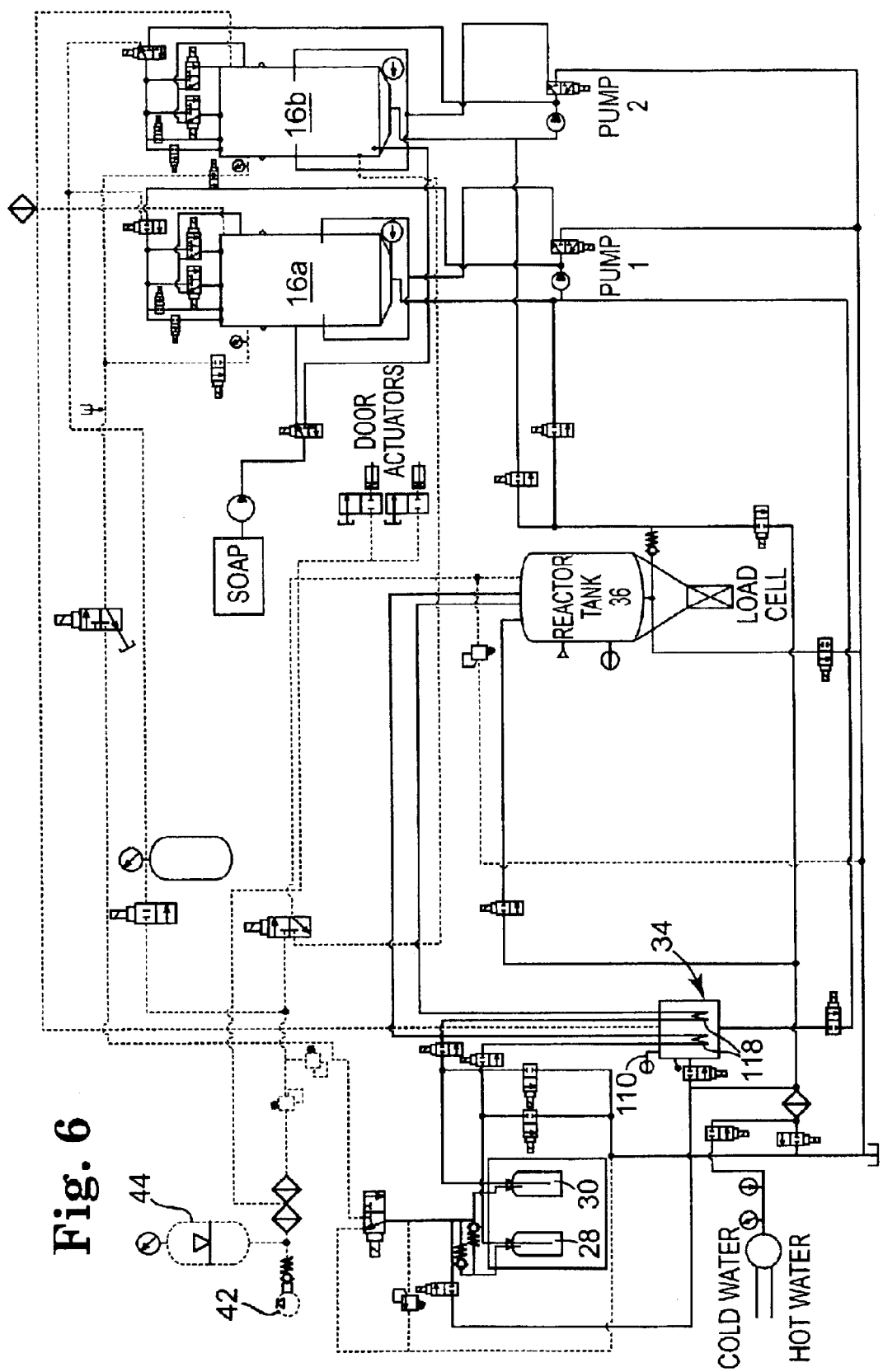
FIG. 6 is schematic representation of a hydraulic system and pneumatic system of a medical device reprocessing device according to one embodiment of the present invention.

Fluid connections between each of the components contained within the drawer 20 and the reprocessing bay 16 contained within the reprocessing bay cabinet 14 are shown only in FIG. 6 to simplify presentation of the major components shown in FIGS. 1–5.

The reprocessing bay 16, in conjunction with the cabinet access door 18, can be constructed so as to provide thermal and sound proofing features as well as an ability to form a pressure chamber. The vertical side walls 48a, 48b, back wall 50, ceiling member 52 and floor member 54 can be formed to provide these features. The thermal and sound proofing features can be provided by manufacturing the side walls 48a, 48b, back wall 50, ceiling 52, floor 54 and door 18 structures of materials such as, for example, plastics, stainless steel, glass and the like. Additionally, the side walls 48a, 48b, back wall 50, ceiling 52, floor 54 and door 18 members can be formed as solid or hollow members and the interior portion of hollow member(s) can be filled with thermal and/or sound insulating materials which are well known in the art.

Figure 3:
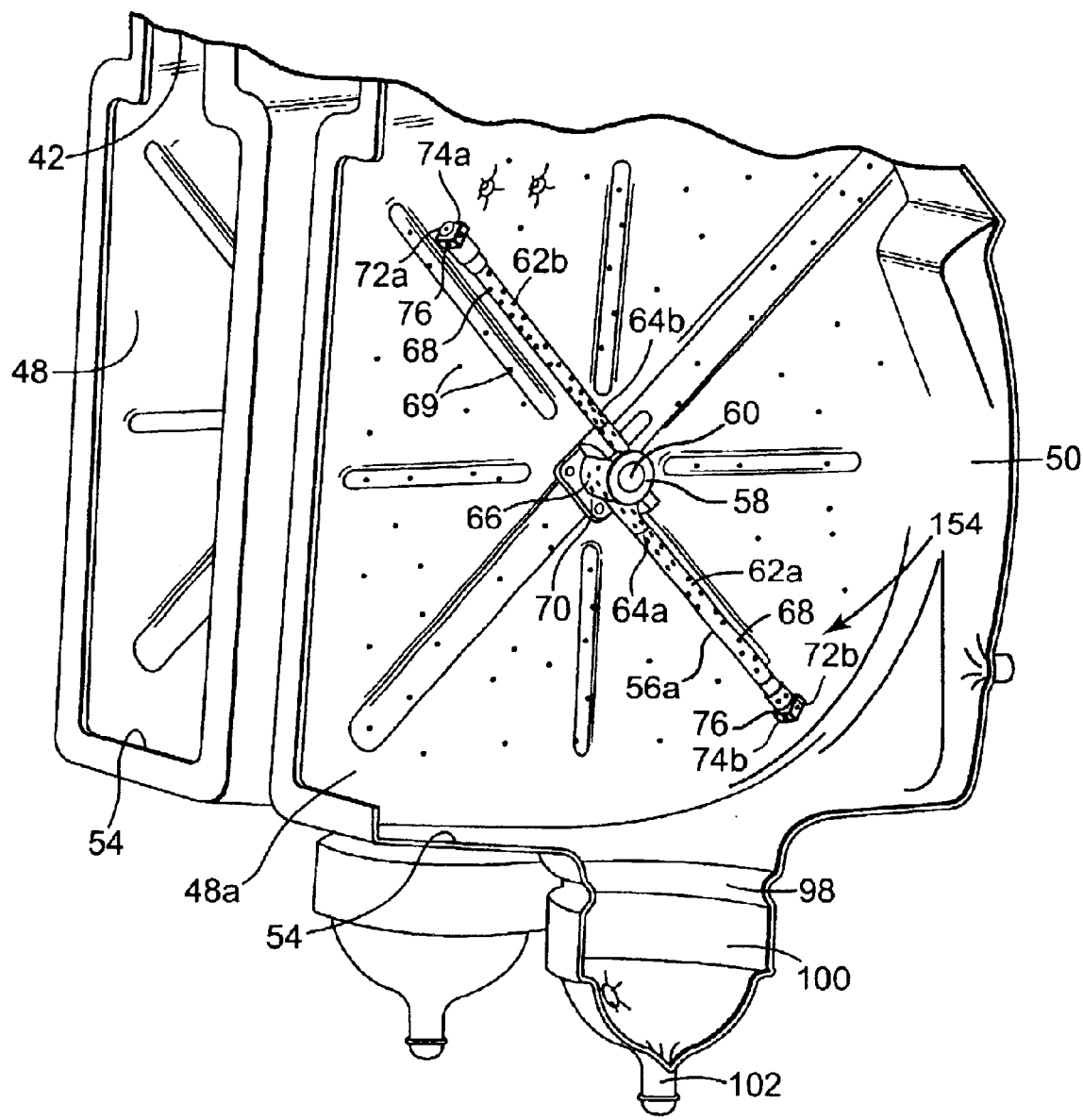
FIG. 3 is a perspective view of a pressure washing assembly, which may be used with the embodiments shown in FIGS. 1 and 2.

The reprocessing bay 16 can be equipped with at least one and more preferably two rotating arm members 56. In the preferred embodiment, the two rotating arm members 56a, 56b are separately rotatably mounted to a central portion of opposing side walls 48a, 48b. The following detailed description applies to all rotating arm members 56 but reference is limited to rotating arm member 56a which is best shown in FIG. 3. The rotating arm member 56a includes a central hub sleeve 58 rotatably connected around a rotating arm hub member 60 which extends outwardly from and substantially perpendicular to the central portion of side wall 48a. At least one and more preferably two counterbalanced sprayers or spray arms 62a, 62b are connected on approximate opposing sides of the central hub sleeve 58 (or could instead or also be located on the top or bottom portion of the bay or both). Each spray arm 62a, 62b defines a spray arm lumen 64a, 64b (shown in part with broken lines). The spray arm lumens 64a, 64b extend at least a portion of the length of the spray arms 62a, 62b and serve to operatively connect a hub sleeve lumen 66 defined within the central hub sleeve 58 with a plurality of spray jets 68 defined in the wall of the spray arms 62a, 62b.

Together the interconnected hub sleeve lumen 66, spray arm lumens 64a, 64b and spray jets 68 provide a conduit for the pressurized flow of washing, rinsing and sterilizing fluids from a rotating fluid connector 70, defined within the hub member 60, to the interior of the reprocessing bay 16. The washing, rinsing and sterilizing fluids are provided to the rotating fluid connector 70 by tubular conduits as shown in FIG. 6. Optionally, one or more of the side walls 48a, 48b, back wall 50, ceiling 52, floor 54 and door 18 members walls of the reprocessing bay can be provided with wall spray jets 69 (stationary or movable) which are fluidly connected to the rotating fluid connector 70 or, alternatively, to a separate fluid inlet connector. Tubular conduits used in the present invention can be formed of metal, plastic, glass and the like, as is well known in the art.

At each distal end 72a, 72b of spray arms 62a, 62b can be a spray nozzle 74a, 74b each configured with a plurality of spray openings 76. The spray openings 76 are operatively connected to the spray arm lumens 64a, 64b and together with the spray jets 68 direct sterilant and rinse fluids into the central portion of the reprocessing bay 16. Alternatively, spray nozzles 74a, 74b may also rotate about the longitudinal axis of spray arms 62a, 62b. In addition to the fluid directing function for sterilizing and rinsing, the spray openings 76 and spray jets 68 direct the pressurized flow of fluid out of the spray nozzle 74a, 74b and spray arms 62a, 62b in such a manner as to effect aggregate impulse which produces a reactive rotational force of the spray arms 62a, 62b around the central hub 60.

The spray arm spray jets 68, spray openings 76 and the wall spray jets 69 may be used to deliver washing, rinsing, drying, or sterilizing fluids to clean the exterior surfaces of a medical device during a reprocessing cycle. A wide variety of fluids may be used, including detergent solution, biofilm-removing solution, chemical sterilant, sterile water, sterile air, water vapor, or steam, for example.

The reprocessing bay 16 may have at least one guide which serves to guide a cassette 80 (e.g., a stainless steel support frame) from a loading and unloading position outside of the reprocessing bay 16 to an operational position inside the reprocessing bay 16. The reprocessing bay 16 may be equipped with guides, an upper guide 78a and a lower cassette guide 78b. The upper cassette guide 78a can be secured to the ceiling 52 or alternatively to the upper portion of the back wall 50 of reprocessing bay 16 or incorporated into the bay design. The lower guide 78b can be secured to the floor 54 or alternatively to the lower portion of the back wall 50 of reprocessing bay 16 or incorporated into the bay design. If the reprocessing bay 16 can be configured to include two cassettes 80 as shown, two sets of guides 78a, 78b can be included, as can door guide 82.

Figure 2:
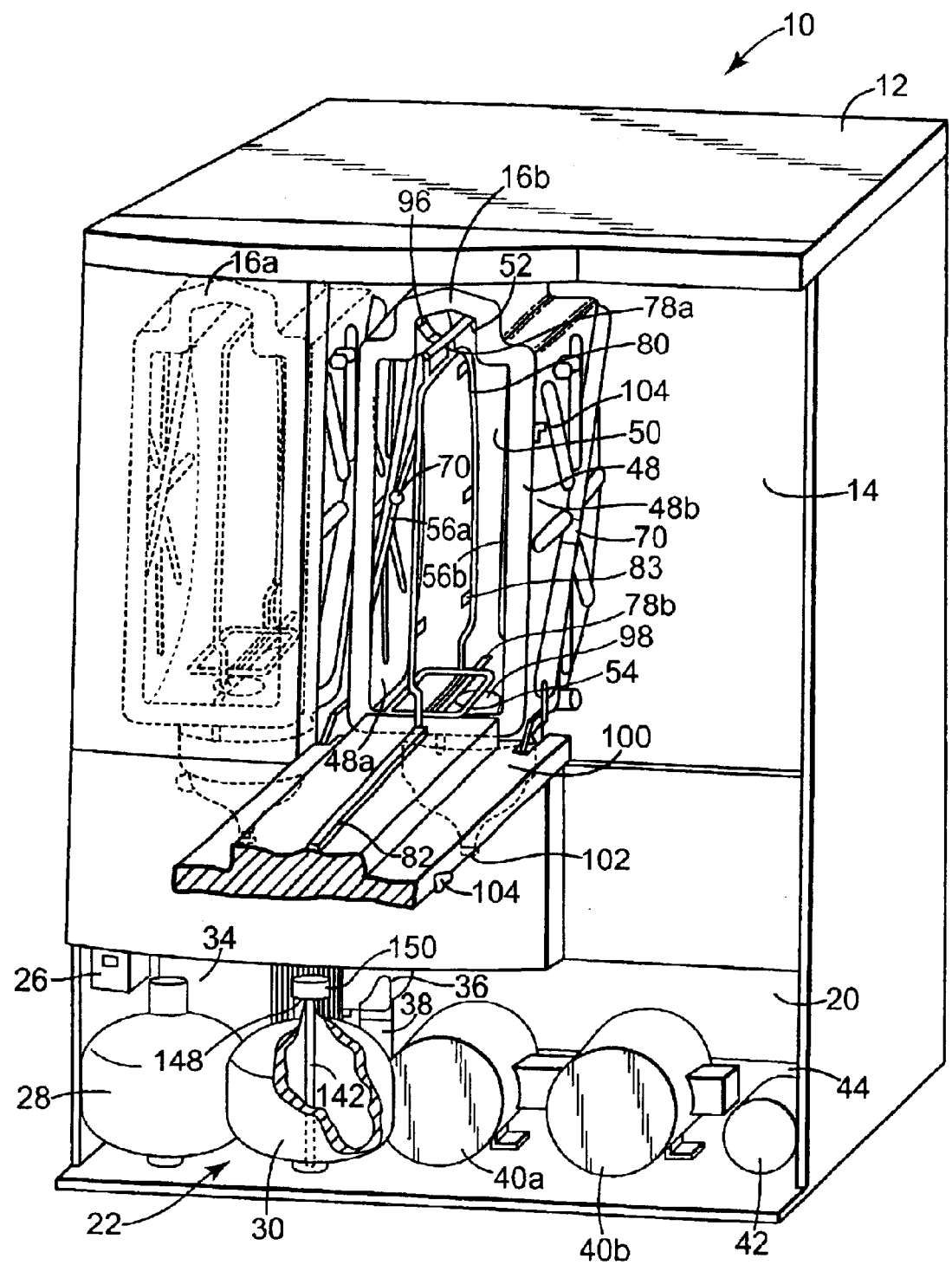
FIG. 2 is a perspective view of, generally the embodiment shown in FIG. 1.
Figure 7:
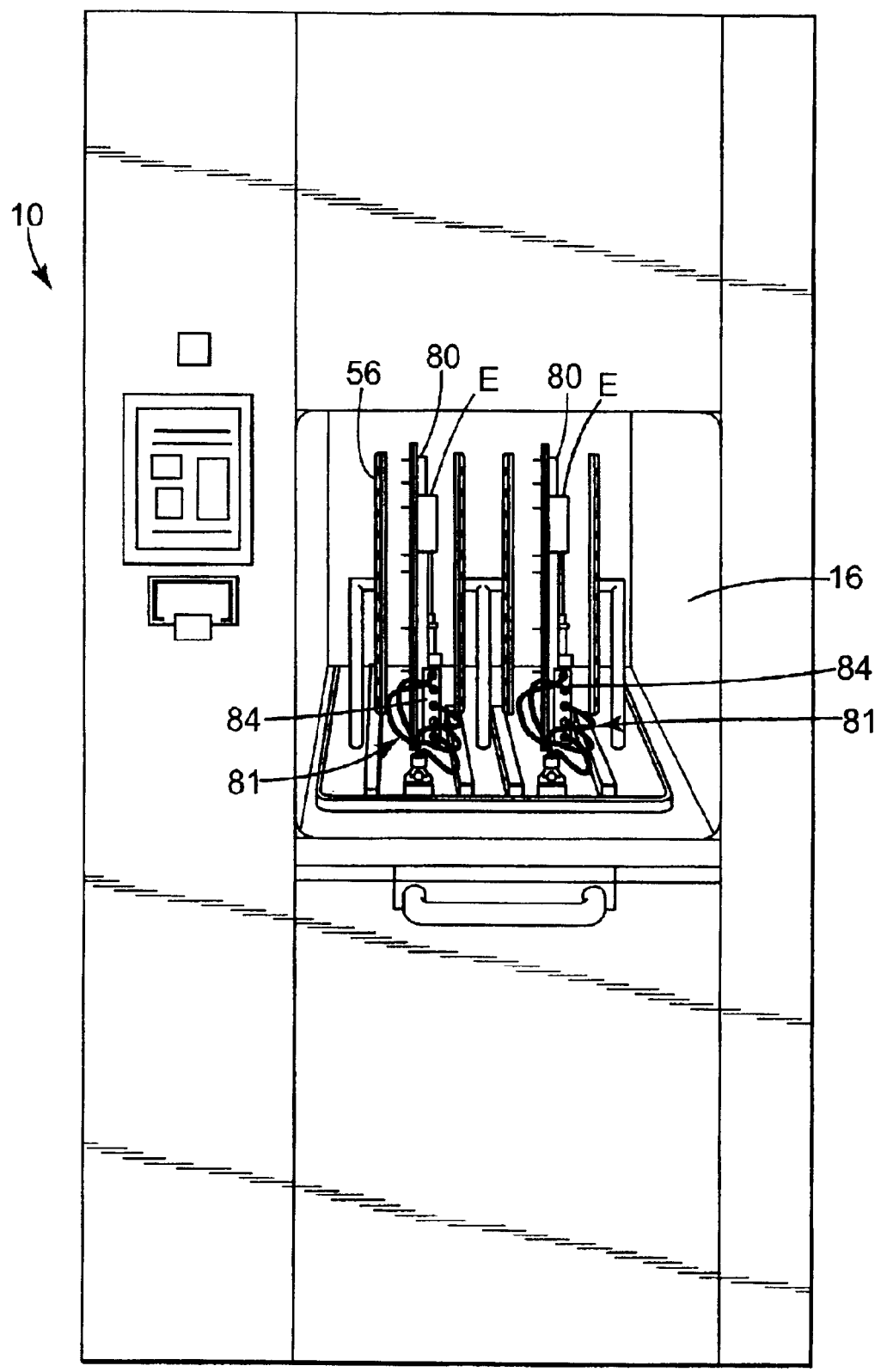
FIG. 7 is an exterior perspective view of an alternative embodiment of the present invention.
Figure 8:
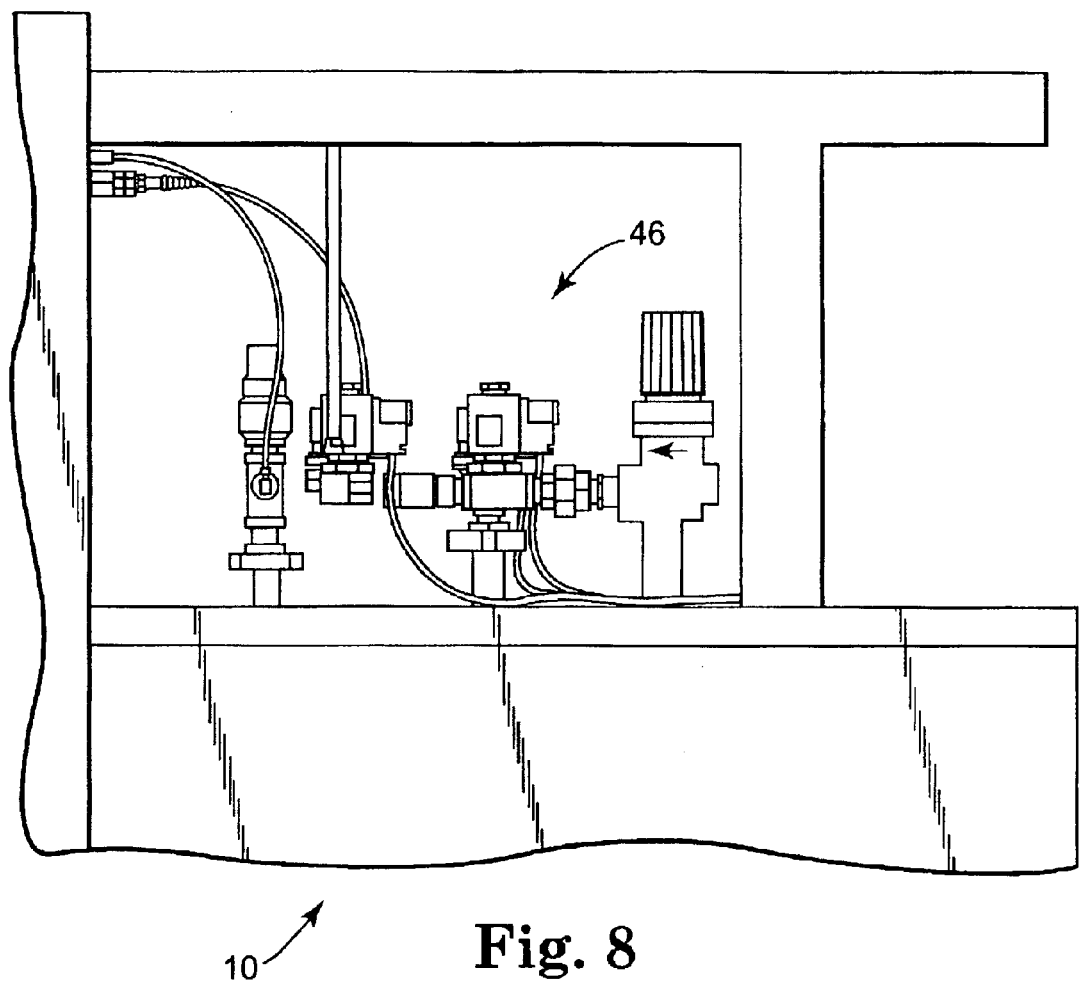
FIG. 8 is a side view of an upper portion or variation of the embodiment shown in FIG. 7, including fluid conduit and valving.

The cassette 80 can be configured to removably secure a endoscope E and a tubing set 81 (shown in FIG. 7) within the reprocessing bay 16. The cassette 80 can be equipped with one or more clamping members 83 for holding the endoscope E being reprocessed in position in the reprocessing bay 16, or may include members around or within which the endoscope E can be removably positioned in the reprocessing bay 16 in a suspended orientation. As shown in FIGS. 2 and 5, the cassette can be preferably removably positioned between the upper guide 78a and the lower guide 78b. As shown in FIG. 5, the cassette 80 may have an upper rotational member 86 and a lower rotational member 88 which are disposed to freely rotate about respective axle members 90a, 90b which are fixedly secured to the upper and lower portions of the cassette 80, respectively. The upper rotational member 86 and the lower rotational member 88, hereinafter referred to as wheels, are each provided with a guiding groove 92, 94, respectively. The guiding grooves 92, 94 are sized and configured to complement the size and shape of the upper guide 78a and the lower guide 78b, respectively, for facilitating movement of the cassette into and out of the reprocessing bay 16.

The cassette 80 can be a stainless steel wire structure. The fluid set 81 can include one or more lengths of tubing, such as a flexible polymeric tubing or a rigid stainless steel tubing. The fluid set 81 can also include a connector manifold 84 into which a plurality of lengths of tubing can be attached. The fluid set 81 can connect ports of the medical device connectors 96 within the reprocessing bay 16 to the one or more openings of the lumen or lumens of the endoscope E. The frame is equipped with clips designed to hold the endoscope such that maximum exposure to fluids or vapor (including steam) are delivered through the rotational members without shielding the endoscope surface from the fluid spray pattern. The frame is constructed from materials which will survive the sterilizer environment without any significant and/or immediate structural or dimensional changes throughout repeated reprocessing. Materials might include, but not be limited, to stainless steel or high performance thermoplastics. The fluid sets can be constructed of materials which will survive the sterilizer environment, yet flexible enough for convenient connecting and disconnecting through multiple reprocessing cycles without failure or fatigue.

Extending into the lower portion of the reprocessing bay 16 can be a medical device connector 96 which can be configured to provide a fluid-tight fitting for a wide variety of medical devices, such as endoscopes. It is within the concept of the present invention to provide connection adapters that will permit a fluid-tight fitting during pressure sterilization of the lumen(s) of a wide variety of medical devices. Washing, rinsing and sterilizing fluids are provided to the medical device connector 96 through tubing conduits as shown in FIG. 6. Washing, rinsing and sterilizing fluids may then be passed or forced into the lumen(s) of a medical device from the medical device connector 96. A wide variety of fluids may be used, including detergent solution, biofilm-removing solution, chemical sterilant, sterile water, water vapor, or steam, for example.

In one embodiment, the system 10 or the endoscope E may be configured so that individual tubing conduits may be separately closed or opened such as by a valve, depending on the requirements of the reprocessing cycle or on the configuration of the medical device to be reprocessed. In another embodiment, outlet ports of the device connector may be separately closed or opened.

In another embodiment, the device connector may be designed to automatically (e.g, a central process program) close or open individual tubing conduits or outlet ports. Closing or opening of tubing conduits or outlet ports may be controlled by a central processor (not shown), for example. (A central processor can be used to control a variety of actions for the system 10.) Alteniatively, the system connector and the medical device may be designed so that coupling of the system and connector can automatically result in the proper conduits or ports being opened or closed. This could be accomplished by providing actuating structure on the device with mating structure on the connector, such tat when the actuating structure and mating structure are coupled the appropriate conduits or ports are opened or closed. Alternatively or in conjunction with the foregoing, the system 10 can be configured to run tests, e.g., pressure tests, to determine which channels or lumens have been made to be communication with, i.e., connected to, the steam source of the system 10 and the system can be configured to either flow steam through all open lumens at once or to selectively flow steam through the open lumens in some other mode, e.g., sequential, alternating, or flowing steam through one lumen for a duration and/or of a heat content that differs from the duration and/or heat content of steam flowed through anpther lumen. Like other actions, this one could be controlled via, e.g, a central processor program. This allows for more control over the processing of die endoscope, which can be important It for example, a portion of the endoscope surrounding or adjacent one lumen is capable of withstanding more heat, pressure, or other condition than a portion of the endoscope surrounding or adjacent a different lumen. The system 10 allows for control over important dimensional changes to the medical device, such as the expansion or contraction of a length, width, height, etc. of a portion of the medical device, as will become more apparent from the remainder of this disclosure.

The floor member 54 of the reprocessing bay 16 can be configured to serve as a reservoir 98 for collection of fluids which have been sprayed onto or pumped through the endoscope E being reprocessed in the reprocessing system 10. The reservoir can be equipped with a filtration system 100 of at least two levels of filtration. A sump drain 102 for collection of fluids can be provided in the lower portion of the reservoir 98. The size of the reservoir 98 and the vertical positioning of the reprocessing bay 16 allows the reprocessing system 10 to operate and recirculate about 2–5 liters of fluid. If the reprocessing system is configured for liquid sterilization, the reprocessing system 10 preferably operates with about 3 liters of liquid sterilant.

In operation of the reprocessing system 10, the reprocessing access door 18 can be selectively secured by at least one latch assembly 104. A safety feature can be provided which will halt operation of the reprocessing system 10 upon opening of the latch assembly 104. Alternatively, the ability to unlatch the latch assembly during operation of the reprocessing system 10 can be disabled until completion of the selected operating cycle.

As shown in FIGS. 2 and 4, the support components 22 located in the drawer 20 facilitate preparation and supply of the fluids used in the reprocessing bay 16 during operation of the reprocessing system 10.

The support components 22 contained within the drawer 20 can include a detergent container 26 which provides detergent or detergent solution to the reprocessing bay 16 as required by the cycle selected.

In the embodiment shown in FIG. 2, two chemical sterilant component containers 28, 30 are provided. The liquid sterilant used in the reprocessing system 10 can be a multi-component concentrate system which can be stored in separate component containers 28, 30 until just prior to use. The concept of the invention is not limited to two-component sterilants but can be adapted as necessary to accommodate a sterilant requiring one, two or more components by merely configuring the device for the appropriate number of component containers. Furthermore, reprocessing system 10 can be configured without any chemical sterilant component containers.

Figure 4A:
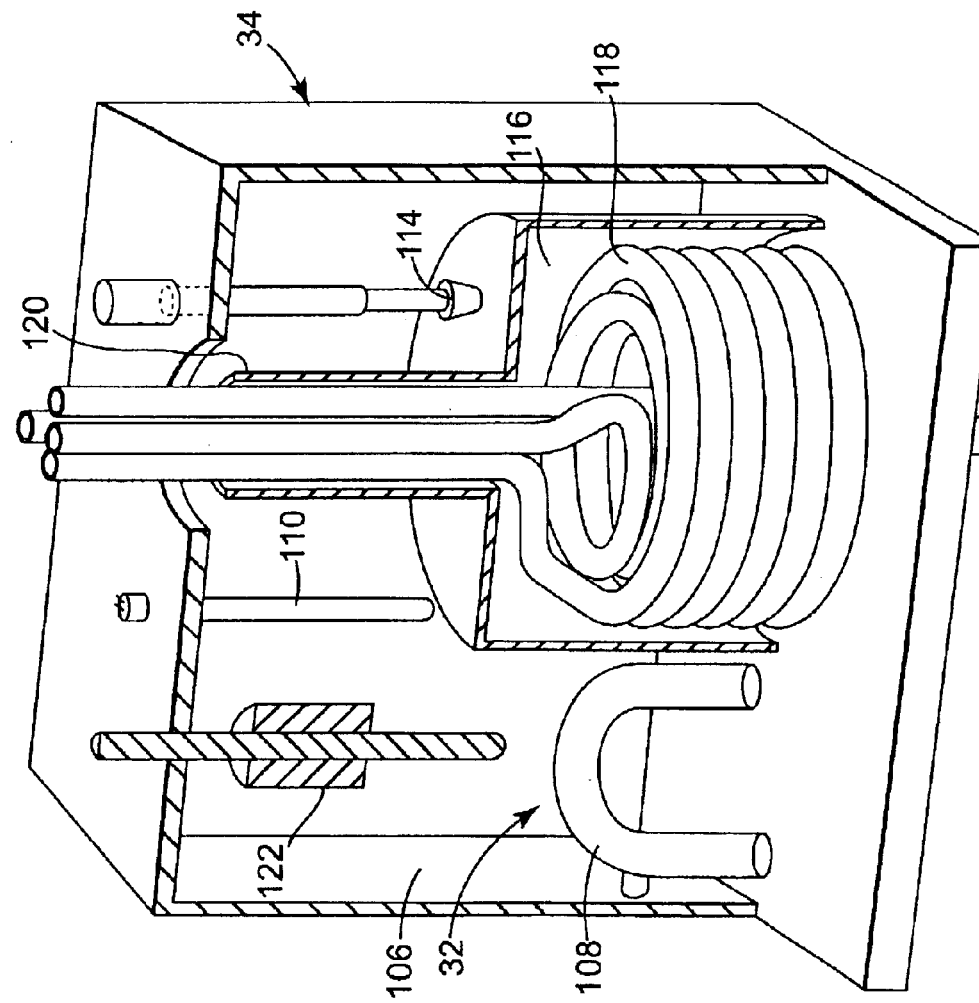
FIG. 4A is a perspective view of a first embodiment of the heating assembly, which may be used with the embodiments shown in FIGS. 1–3.

As shown in FIG. 4A, in a first embodiment, a water heater and a water tank are further provided in the reprocessing system of the invention for heating fluids for use in the reprocessing cycle and/or for heating the chemical sterilant or chemical sterilant components therefore. In that regard, the reprocessing system is compatible with caustic sterilant or chemical sterilant components for use in a reprocessing cycle. Thus, the chemical sterilant or chemical sterilant components can be flowed through a closed conduit system to and among the components of the reprocessor.

Furthermore, the temperature of the chemical sterilant components may be maintained at an elevated level prior to delivery to the reaction chamber, and the temperature of the sterilant may be maintained at an elevated level prior to delivery to the reprocessing bay(s). To do so, the conduit through which the sterilant or chemical sterilant components flow preferably passes through the water tank to define a heat exchanger. Additionally, a cooling coil could be provided within the heat exchanger so that temperature ramps could be accurately controlled. A circulation device may also be included within the heat exchanger to circulate a heat-exchanging fluid within the heat exchanger. Other means for changing temperature are contemplated. A temperature sensor connected to a central processing unit may also be included.

Thus, in accordance with one first embodiment, shown in FIG. 4A and described in greater detail below, the heater 32 and tank 34 can be provided as a combination unit with coiled tubing for heat exchange disposed therein. When combined, the heater and hot water tank can serve multiple purposes. First, the water heater can be used for heating water which can be subsequently used in the detergent cleaning phase of the reprocessing cycle as well as in the sterilant dilution phase of sterilant preparation in the reaction chamber 36. The water heater and hot water tank can also be used as a heat exchanger to heat the chemical sterilant components during transfer to the reaction chamber 36 and/or, subsequently, to maintain the sterilant at, or about, the optimum operating temperature prior to use. As yet a further alternative, however, the reprocessing system 10 can be adapted to operate with room temperature fluids, thus eliminating the need for the water heater and hot water tank.

With reference to FIG. 4A, a first embodiment of a combined water heating coil 32 and hot water tank 34 is shown. More particularly, the assembly includes a water tank 106 which serves to contain and insulate water pumped into and heated in the hot water tank 34. A controlled heater element 108 can be provided to initially heat and thereafter maintain the temperature of the water in the water tank 106. A temperature sensor or probe 110 can be provided to measure the temperature of the water in the tank and transmit that information to a central processor. An inner tank valve 114 can be provided on the upper surface of an inner tank 116. The inner tank valve 114 may be temperature sensitive or preferably can be controlled by the central processor from information received from the temperature probe 110. The inner tank 116 can be configured to enclose chemical sterilant component containing coils 118 which act as conduits to transport the chemical sterilant components to the reaction chamber 36 creating sterilant, which may then be transported on to the reprocessing bay 16.

An upper rim 120 of the inner tank 116 extends above the water level of the water tank 106 and serves to keep water from prematurely entering the inner tank 116. A water level sensor 122 can be provided to determine the amount of water in the water tank 106. The water level information can be provided by the water level sensor 122 to effect a cut off of water flow into the water tank 106. The water level sensor can be configured to sense a high water condition and stop water flow into the water tank 106 prior to the water level going above the upper rim 120 of the inner tank 116. This protective feature is able to keep water that has not reached a target temperature or temperature range, which in the first embodiment is about 40° C. to about 55° C., from entering into the inner tank and undesirably cooling the coils 118 and chemical sterilant or chemical sterilant components contained therein to a temperature below the target range. In the embodiment illustrated in FIG. 4A, two coiled tubes 118 extend into the water tank 106, e.g. one for each chemical sterilant component. When the temperature of the water in the water tank 106 reaches the most preferred temperature of e.g. about 40° C. to about 55° C., the inner tank valve 114 opens to permit the warm water to drain from the water tank 106 into the inner tank 116. The warm water fills the inner tank and serves to maintain the coils and enclosed sterilant or chemical sterilant components at the most preferred operating temperature prior to mixing in the reaction chamber 36.

Figure 4B:
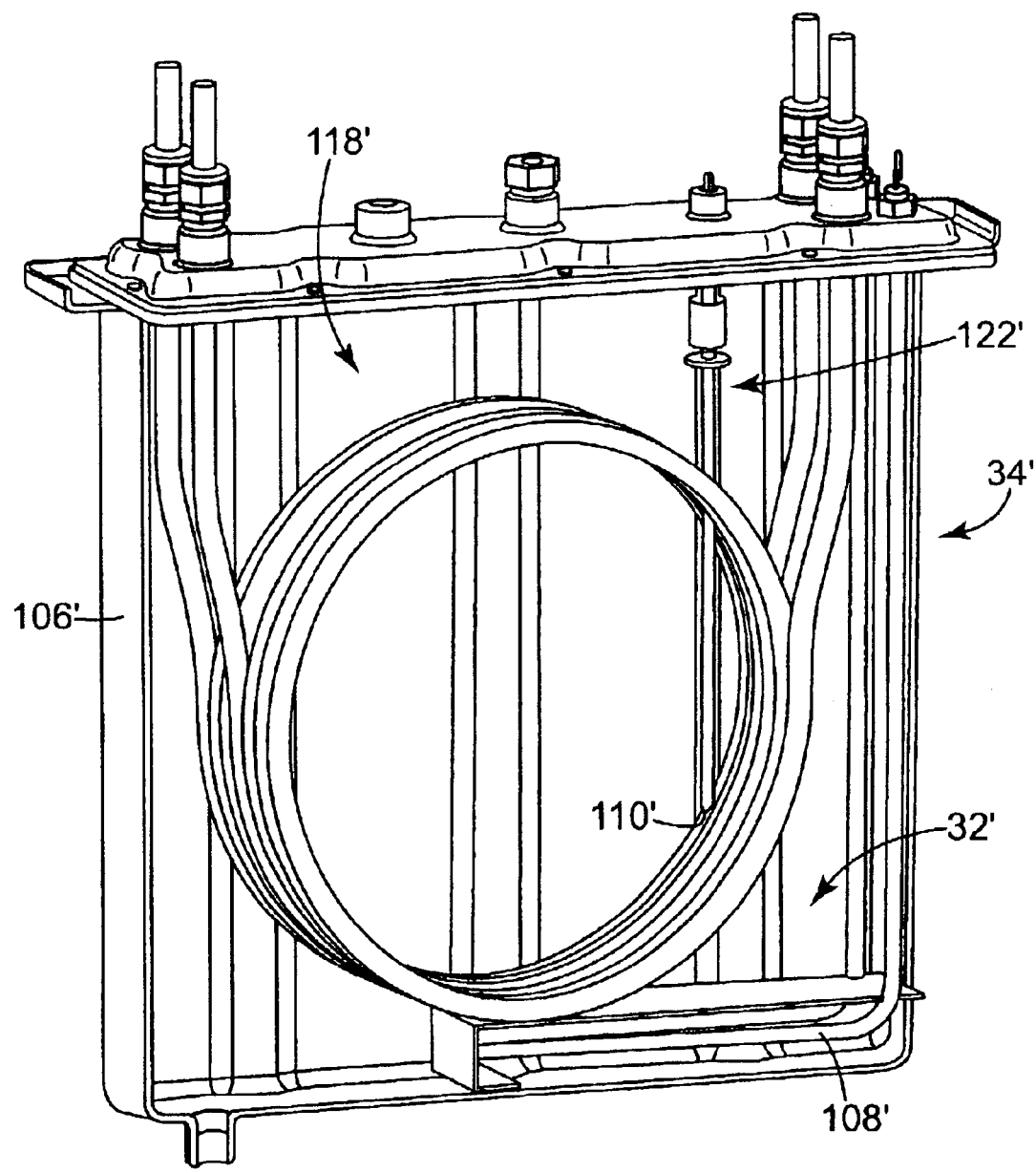
FIG. 4B is a perspective view of a second embodiment of the heating assembly, which may be used with the embodiments shown in FIGS. 1–3.

With reference to FIG. 4B, a second, and presently preferred, embodiment of a combined water heating coil 32' and hot water tank 34' is shown. More particularly, the assembly includes a water tank 106' which serves to contain and insulate heated water pumped into the hot water tank 34'. Heated water can be received through a mixing valve that automatically (or via, e.g., a central processor program) mixes hot and cold water to obtain the desired temperature water. A controlled heater element 108' can be provided to maintain the temperature of the water in the water tank 106'. A temperature probe 110' may be provided to measure the temperature of the water in the tank and transmit that information to a central processor. In contrast to the embodiment of FIG. 4A, no inner tank is provided in the hot water tank 34'. Thus, the fluid in the coiled tubes 118', which may be chemical sterilant components prior to delivery to the reaction chamber 36 or sterilant prior to delivery to the reprocessing bay 16, will be heated according to the temperature of the water in the tank 106'. A water level sensor 122', such as a float switch, can be further provided to effect a cut off of water flow into the water tank 106' or initiate flow thereto.

The reaction chamber 36 in the preferred embodiment of the present invention can be positioned upon and supported by a load sensor 38. It is, however, within the concept of the invention to secure the reaction chamber 36 in the reprocessing system 10 by suspending it below or supporting it on a load sensor 38. The chemical sterilant components can be provided to the reaction chamber 36 incrementally so as to enable the load sensor 38 to determine the precise amount of each component transferred to the reaction chamber 36 as the transfer takes place. In the preferred embodiment, the reaction of the chemical sterilant components can be allowed to take place. After sufficient reaction time, the correct amount of water can be weighed into the reaction chamber 36 based upon the measurements obtained from the load sensor, to properly dilute the sterilant prior to use. Accuracy of the load sensor 38 can be critical to proper mixing of the components of the sterilant. The load sensor 38 of the present invention can be configured to prevent shifting of the reaction chamber 36 from affecting the load sensor measurements. While some vertical movement can be permitted and does not affect the load sensor measurements, the load cell of the present invention can be configured to maintain horizontal stability by a supporting strap located on top of the reactor vessel. The load cell of the present invention may be equipped with a test feature to ensure consistent and correct readings. The load sensor 38 may be checked for zero load when the reaction chamber 36 is empty. The load sensor 38 may also be checked against a known volume and weight of a specific volume of water, such as the volume of the inner tank 116.

An embodiment of the reprocessing system 10 that relies primarily on liquid sterilants can operate with sterilant temperatures from about 20° C. (room temperature) to about 50° C. More preferably for this approach, the temperature range can be from about 40° C. to about 50° C. The chemical sterilant components may be heated and reacted at higher temperatures. However, temperatures higher than about 50° C. in the reprocessing bay(s) may cause damage to the endoscopes. As noted above, temperature and/or level sensors can provide the information measurements to the central processor and thus enable the automatic or programmed drainage and refilling of the inner tank throughout the selected cycles of operation of the reprocessing system 10, thus maintaining the temperature of the sterilant at a temperature of from about 40° C. to about 50° C. The central processor may be programmed with a maximum permissible temperature for the instrument being reprocessed, and programmed to discontinue the application of heat during any cycle if the maximum permissible temperature is approached or exceeded.

Circulation of the various solutions used in different cycles of the reprocessing system 10 can be performed by an electric motor and pump 40. It is, however, within the conception of the present invention to configure the device to use gravity flow for the transfer of some fluids in the reprocessing system, for example water flow to the reaction chamber for dilution of the sterilant. In the preferred embodiment of the present invention, the reprocessing bay 16 can be provided with a dedicated electric motor and pump 40. It is, however, within the scope of the invention to configure the reprocessing system 10 such that the central processor could effect a time sharing of electric motor and pump 40 assets for systems having a larger number of reprocessing bays than that of the preferred embodiment. However, time sharing would increase the overall processing time. Central processor control of solution transfers throughout the selected cycles can be affected by fluid conduit and valve systems known in the art; to include, for example the use of solenoid valves. FIG. 6 provides a detailed schematic of an exemplary fluid system of an embodiment of the present invention.

In one embodiment of the reprocessing system, delivery of the components of the sterilant into the reaction chamber 36 can be accomplished using compressed air. An air compressor 42, under control of the central processor can be provided for purpose of maintaining the air pressure in a compressed air tank 44. On command of the central processor, compressed air from the compressed air tank 44 can be provided to the chemical sterilant containers 28, 30 in a programmed order so as to transfer each component to the reaction chamber 36 with the greatest precision. Alternatively, air pressure may be maintained on the chemical sterilant containers 28, 30 and, instead, the central processor controls valving in a programmed order so as to transfer each component. The load sensor 38 controls the information input to the central processor which in turn controls the output of the chemical sterilant containers 28, 30. FIG. 6 also provides a schematic of an exemplary pneumatic system of an embodiment of the present invention.

The present invention can be provided with a chemical concentration detector for determining the concentration of sterilant in the reaction chamber 36. Suitable chemical concentration detecting systems are described, for example, in U.S. Pat. No. 6,068,815 to Oberleitner, et al., the entire disclosure of which is hereby incorporated by reference. Also, a chemical sterilant component container validation system may be provided, such as the system described in U.S. Pat. No. 6,068,815.

The present invention can include chemical sterilant containers 28, 30 which can be designed to respond to pneumatic force for transfer of the components to the reaction chamber 36 and from the reaction chamber 36 to the reprocessing bay 16. As best shown in the cutaway portion of the chemical sterilant container 30 in FIG. 2, the design of the chemical sterilant containers 28, 30 includes an internally positioned straw tube sipper 142. The tube sipper 142 extends to the bottom of the chemical sterilant container 30 while the top of the sipper tube 142 fits into a straw header which in turn fits into the neck of the chemical sterilant container 30. When preparing the chemical sterilant container 30, the chemical component can be filled into the chemical sterilant container 30 and a foil seal cap 148, which may include a vented membrane, can be placed on the chemical sterilant container 30, and sealed with induction energy to prevent leaks.

When preparing for use in the reprocessing system 10, the user removes the cap 148 exposing the membrane seal which can then be punctured with a spike in the screw-on connector assembly 150. A gasket in the cap seals the connector assembly 150 to the chemical sterilant container 30. The spike of the connector assembly 150 makes two fluid connections to the chemical sterilant container 30, one concentric through the straw header 144 and the other eccentric outside the tube sipper 142. The spike of the connector assembly 150 can be operationally connected to two tubing lines in the reprocessing system 10. The chemical can be removed from the chemical sterilant container 30 by forcing air pressure into the chemical sterilant container 30 through the eccentric connection. This forces the chemical component up through the tube sipper 142 and into the tube running to the reaction chamber 36. When the chemical supply in the chemical sterilant container 30 is exhausted, the air supply tube can be used to put water into the chemical sterilant container 30. This washes the top connection area as well as the chemical sterilant container 30 sides and tube sipper 142 to remove residual chemicals. This flushing process can be repeated, as necessary to remove the residual chemicals from the chemical sterilant container 30.

Chemical components for the sterilant can be heated and measured as they are moved to and mixed in the reaction chamber 36. The sterilant temperature can be monitored and controlled and the reaction of the chemical components in the reaction chamber 36 can be timed under the control of a central processor. The sterilant's refractive index can be measured to verify the presence of the sterilant. Water can be added to dilute the sterilant to the use-dilution concentration. The endoscopes can be mounted on the cassettes 80 and connected to the medical device connector 96 through which the lumen of the endoscope will be pressure washed and sterilized. The reprocessing access door 18 can be secured, and the endoscopes can be internally and externally washed with detergent and water and rinsed.

As previously noted, the chemical sterilant can be replaced by or used in conjunction with a steam sterilization approach using, for example, embodiments shown in FIGS. 7–10. Much of the previous disclosure could, therefore, involve the use of steam in place of the liquid sterilant. A steam source 46 can deliver steam to the reprocessing system to disinfect and/or sterilize the exterior and interior of the endoscope E. Such delivery can come to the system 10 through the conduit and/or valving shown in FIG. 8, including the chamber steam pressure release safety valve, steam-to-jacket solenoid valve, steam-to-chamber solenoid valve, steam pressure regulator, and wiring to solenoid valves. Though FIG. 9 illustrates conduit and valving (e.g., drain line, solenoid gasket drain vent, gasket pressure switch) for draining liquid from reprocessing bay 16), this lower portion of the system 10 could include the steam source. Conduit and/or valving in the lower portion of system 10 can also or instead be used for removal of liquids from the reprocessing bay 16, such as the conduit and valving shown in FIG. 9.

Steam, for example, at a temperature of about 121 degrees Celsius can be used, or it may be at higher or lower temperatures as is desired to affect the cycle time and heat shock upon the endoscope E. (Heat or thermal shock, which can be avoided or reduced by using the system 10, is used herein to refer to harm or damage to a material or component of the medical device due to an excessive heat transfer rate or thermal expansion or contraction rate of a material due to heat or unequal or incompatible thermal expansion/contraction rates of adjacent materials or components. Similar to avoiding or reducing heat shock, the system 10 can be useful to avoid or reduce damage to thermally expanding or contracting components having limited clearance therebetween by controlling such expansion or contraction through the structure and methods referred to herein.)

Typical steam sterilization cycles conditions can be about 270° F./132° C. for a vacuum assisted steam sterilization process or about 250° F./121° C. for a gravity displacement steam sterilization process. More broadly, the range of steam can be, for example, from about 115° C. to about 126° C. or from about 121° C. to about 140° C. (although this or any other temperature range noted herein must be considered together with reprocessing time, degree of bioburden, sterilization test results, and other factors before a determination of sterility, disinfection, decontamination or the like can be made). The steam autoclave can comprise a steel shell (to form the bay) equipped with a sealable door on one end and a thermally controlled jacket surrounding the main shell. The surrounding jacket can be fed with hot or cold water, hot or cold air, steam or steam and water mixtures. The main shell can contain moving arms 56 which can be fed by cold or hot air, cold or hot water containing or not containing detergents or biofilm removers, steam, steam and water mixtures. The endoscope manifold 84 can be connected to described source(s) of hot or cold air, hot or cold water containing or not containing detergents or biofilm removers, steam, dry steam, steam and water mixtures, or a source of alcohol or the like for final drying of the endoscope inner channels or lumens.

The source of steam for sterilizer jackets, sterilizer bays and endoscope manifolds can be fed through control valves linked to pressure sensors, safety relief valves and temperature sensors. Temperature sensors can be positioned so as to monitor temperature at various locations within the sterilizer chamber, on the sterilizer jacket, in the endoscope connector manifold, and on or in the endoscope. A self-contained, on-board steam generator or a central source of or "house" steam can be utilized to heat and to sterilize the medical device. The steam sterilizer can typically be equipped with a vent drain line to remove water which will condense from the saturated steam within the sterilizer chamber or bay. After the endoscope inner channels or lumens, exterior surfaces and sterilizer chamber can be heated to a temperature of approximately 270° F./132° C., a source of saturated steam may provide the most efficient sterilization. Steam quality is typically expressed as a percentage of dry saturated steam versus entrained water. Efficient removal of air from the sterilizer immediately-preceding the terminal sterilization phase of the cycle can be important for highest steam quality which should approximate 100% under ideal conditions.

It is contemplated that two or more steam sources 46 may be used as means for quickly or controllably changing the temperature (or other quality or aspect, e.g., flow rate, moisture content) of the steam being applied to the endoscope E. This can be one approach for controlling the heat-up and cool-down of the materials that make up the endoscope E, though other known approaches for heating and cooling are contemplated. The flow of liquids can be used to control heat-up and cool-down as well, as can other heating and cooling approaches.

Rather than to rely entirely on a steam, or more specifically a high temperature steam, sterilization approach, a lower temperature steam mixed with formaldehyde (or another gaseous sterilant) can be used within the reprocessing system. Typically, formaldehyde gas is injected into the chamber at subatmospheric pressure and followed by steam injections. An advantage of the low temperature steam formaldehyde approach is that aeration times are less than ethylene oxide sterilization which can last as long as 24 hours. Low temperature steam formaldehyde sterilization requires that users monitor both the environment and sterilized medical devices for residual formaldehyde.

Similarly, it is contemplated that a sonicator (not shown) be included within the reprocessing system 10 as a means for affecting the quality of the steam or as a means for providing a water vapor (non-steam). This too can be used for controlling the heat-up and cool-down.

If necessary, just prior to the sterilization cycle, the endoscopes may be rinsed with warm or hot water to ensure the sterilant will not be excessively cooled upon contact with the endoscopes. The endoscopes can then be sterilized internally and externally with sterilant prepared in the reaction chamber 36 just prior to use or with steam sterilant. The cleaning and sterilization of the endoscope lumen through the medical device connector 96 can be assisted by a flow of liquid (detergent and water, rinse water, and sterilant in turn). The cleaning phase receives a superimposed pulsating flow of air. This pulsating flow of air causes the liquid flow to become severely unsteady, resulting in a scrubbing action on the lumen wall of the endoscope.

During operation of washing, sterilizing, or other steps, the present invention can detect if the wash bay is in an overflow condition. The reprocessing bay 16 and the rotating arm members 56a, 56b can be equipped with a speed sensing assembly, generally indicated at 154. The speed sensing assembly can include magnets positioned on one or more of the rotating arm members 56a, 56b and Hall Effect sensors located in the side walls 48a, 48b. When the reprocessing bay 16 is in an overflow condition due to an over accumulation of liquid in the reprocessing bay 16, the rotational speed of the rotating arm members 56a, 56b will slow. The Hall Effect sensors, which can sense the frequency of passage of the rotor arm magnets, transmits a frequency signal to the central processor which in turn can provide an overflow message to the user interface.

The reprocessing system 10 of the present invention can include a block detection feature which can be coordinated and interpreted by the central processor. A central processor (not shown) of the system 10 can release a specific known volume and pressure of air from an air reservoir, preferably a separate 4 liter air reservoir, and the central processor can monitor air pressure through the lumen of the endoscope channels by use of a pressure sensor which can provide a steady flow of information to the central processor. Blockage of channels within the endoscope can be determined by changes in pressure or flow rate from established acceptable values and characteristic pressure drop curves. The central processor, upon determining a blockage, can terminate the operation and present a blockage message to the user interface 152.

The reprocessing system 10 of the present invention can include a leak detection feature that can be coordinated and interpreted by the central processor. The central processor can pressurize the endoscope jacket with a known air pressure and the central processor monitor the air pressure loss by use of a pressure sensor that can provide a steady flow of information to the central processor. Leakage can be determined by changes in pressure from acceptable values or characteristic pressure drop curves. The central processor upon determining leakage can terminate the operation and present a leakage message to the user interface 152. Air pressure can be maintained in the endoscope jacket during reprocessing to protect the endoscope jacket and its contents from exposure to fluids.

A self-cleaning feature of the reprocessing system 10 can be accomplished by a self-sterilization cycle controlled by the central processor which controls the pumping of fluid through tubing lines which can harbor bacteria. The reaction chamber 36 can be connected to the water lines which are used for washing the endoscopes as well as rinsing the endoscopes. The flushing of these potential harbors for the growth of bacteria in the self-sterilization cycle maintains the reprocessing system 10 of the present invention in safe working order.

Operation of the reprocessing system 10 can be monitored by sensors, including those described above, which provide information to the central processor. The central processor receives cycle program instructions from a user, including endoscope identification through the user interface 152. The user interface can be equipped with any form of command signal keys or buttons as is well known in the art. Visual displays of user commands which are entered, such as with a touch screen, as well as central processor responses, error messages, status notifications and the like can be presented to the user at the user interface 152. A printer capability can be included to permit the central processor to provide written records of any aspect of reprocessing system operation to the user. Printed records of specific endoscope sterilization can also be printed at the completion of a reprocessing and sterilization cycle. All aspects of the operation of the reprocessing system 10 can be controlled by the central processor, to include measuring and mixing of chemical sterilant components for the sterilant, metering of water to the reaction chamber 36 for sterilant dilution purposes, washing, rinsing and sterilizing cycles, self-sterilizing, blockage detection and user notification, door ajar sensing and responsive operation termination, and other similar system monitoring and operational controls.

The central processor can also be programmed to memorize the appropriate settings for a given model of scope, so that reprocessing parameters would not need to be entered by an operator. Furthermore, the central processor could be programmed to track the number of reprocessing cycles that a specific individual device has experienced, and notify the operator when a threshold number of cycles has been reached. This feature ensures that a device is not exposed to more reprocessing cycles than is recommended by the manufacturer.

The electrical requirements for the reprocessing system 10 are provided so as to ensure a constant RPM for the electric motors and pumps 40, regardless of the input line frequency (50 or 60 HZ). AC motor speed can be influenced by the input line frequency. In the present invention, using a solid state inverter circuit, which is commercially available, the single phase input power can be converted to 3-phase power for the electric motor 40. The inverter converts the input AC power to DC and then reconverts the DC power to 3-phase AC power. This power supply process provides for electric motor and pump 40 operation which can be insensitive to the input line frequency.

As previously noted, the present invention further provides methods for cleaning, disinfecting, and/or sterilizing sensitive medical apparatus such as flexible endoscopes. The methodology disclosed above and below refer to several steps. Many combinations of these steps are contemplated as part of the present invention.

In one embodiment, the reprocessing system 10 described above can be used by an operator for reprocessing a device D. The operator can attach the device D to a cassette 80, insert the cassette 80 into the reprocessing system 10, and connect the device D to the reprocessing system 10 via the device connector 96. The bay 16 with door 18 provides a sterile barrier to seal off the internal region of the system 10 from areas external to the system 10. The operator can activate any necessary interlocks or other safety features. The operator may then initiate a reprocessing cycle (manual, automatic, or semi-automatic). A reprocessing cycle may be initiated using, for example, the control panel on the system 10 or by issuing a command to the central processor.

The endoscope E can first undergo a precleaning step in which the exterior of the device or an interior lumen are rinsed or flushed with water. Prior to the precleaning step, it may be desirable to perform a pressure test or leak-checking step, as described above. In the event of a failure, the reprocessing cycle is discontinued and the operator is notified.

After precleaning, the device can be cleaned with a liquid detergent solution or biofilm removing solution. Then, the endoscope E can be rinsed to remove residual material as well as remaining detergent and biofilm removing solutions.

A drying step can be carried out. Drying of the exterior or lumen of the device may be accomplished by a variety of methods. For example, drying of the lumen may be achieved by cycling dry sterile air or other dry sterile gas through the lumen, preferably at an elevated temperature. Alternatively, a low-boiling liquid such as alcohol could be cycled through the lumen to remove water, followed by purging of fluids and subsequent evaporation of any remaining liquid. As a third option, rinsing fluid may be purged from the lumen, followed by application of vacuum to the lumen to evaporate any remaining fluid.

The device E can be sterilized by exposing the device to one or more of the previously noted sterilants. For example, higher temperature steam can be directed against the exterior of the endoscope E and flowed through the lumen(s) thereof. Alternatively, at least a portion of the device can be exposed to lower temperature steam containing a chemical agent such as formaldehyde.

Alternatively, a chemical sterilization step may be used in place of or in conjunction with steam sterilization. For example, a chemical sterilant may be introduced to the lumen or exterior region at the outset of the sterilization step, followed by application of steam to increase the temperature. This procedure may result in a higher chemical activity of residual chemical sterilant on or within the device, due to the increase in temperature. A reduced cycle time may thus be achieved by a combination of chemical sterilization and steam sterilization. Alternatively, introduction of a chemical sterilant could follow steam sterilization. In this embodiment, a chemical sterilant fluid could be introduced at a slightly lower temperature to initiate a cooldown of the device.

After the sterilization step, an optional drying step may be carried out. Drying of the exterior or lumen of the device may be accomplished by a variety of methods. For example, drying of the lumen may be achieved by cycling dry sterile air or other dry sterile gas through the lumen, preferably at an elevated temperature. Alternatively, a low-boiling liquid such as alcohol could be cycled through the lumen, followed by purging of fluids and subsequent evaporation of any remaining liquid. As a third option, vacuum may be applied to the lumen to evaporate any remaining fluid. (The application of a vacuum, i.e., reduced pressure source, can occur through the use of a house vacuum system, an onboard vacuum pump, or the like.)

After a sterilization step that includes the significant heat-up of the endoscope E, another step can be to cool-down the endoscope E to enable the operator to more easily remove the endoscope E from the reprocessing system 10. Approaches for heating up the endoscope E can effectively be reversed to cool down the endoscope E. Alternatively, a vacuum could be pulled within the bay 16 or the liquid could be sprayed onto and/or flowed through the endoscope E (e.g., sterile water, alcohol/water solution, and the like).

As noted above, during one or more of the various reprocessing steps, certain limitations should be observed with respect to the treatment of delicate devices. It is desirable to heat the device (if heat is needed) to a temperature sufficient to sterilize the device, but too extreme a temperature may damage components of the device or may destroy materials such as plastics. Also, to avoid thermal shock it is often necessary to heat or cool certain components or materials of the device at sufficiently slow rates. High heating or cooling rates may adversely affect the lifetime of the device. On the other hand, it is desirable to perform a reprocessing cycle as quickly as possible to ready a device for another procedure and to make the reprocessing system available for the reprocessing of another device.

For example, as part of the precleaning step, it may be desirable to gradually expose portions of the device to an elevated temperature. This may be done by, for example, a pre-rinse by cycling fluid through a lumen of the device or spraying fluid onto the exterior of the device, where the fluid is at a somewhat higher temperature than the contacted surface. The pre-rinse may serve an additional purpose of removing or dislodging any biomaterial remaining on or within the device. Water or sterilized water is a suitable fluid for the pre-rinse, for example. The system 10, as a result, could be used to replace manual pre-rinsing, pre-washing, and the like.

Gradual warming of the device during precleaning may be achieved by exposing the device to a sequence of fluids that, for example, are incrementally changed in temperature, or by continuously changing the temperature of a fluid to which the device is continually exposed. Optionally, the temperature of the device may be brought to a temperature at or near a temperature that is desired during the remainder of the precleaning step. The rinsing fluid, used after the precleaning or cleaning step, could likewise be adjusted to a temperature at or near the temperature of the device, to avoid thermal shock.

During the course of the rinsing step, it may be desirable to further adjust the temperature of the device by gradually or incrementally increasing the temperature of the rinsing fluid. Where the device is to be next exposed to steam, it is recommended that the rinsing step be carried out to bring the temperature of the device to a temperature near the temperature of steam to be used.

During the course of applying steam to the endoscope E, the temperature of the steam can be increased during the "heat-up" and/or decreased during the "cool-down." Steam sterilization has been optimized in terms of equipment and process conditions to minimize the overall cycle time. One measure of "inefficiency" is the time required for the internal temperature of a wrapped "pack" of medical devices and the sterilizer chamber to reach the same temperature. Typical times required for temperature equilibrium between pack and chamber are on the order of 6 to 12 minutes, depending on the chamber pressure. Use of lower pressures or use of pulsing pressure cycles will shorten the time to equilibrium. Chamber pressures below 20.0 mm Hg will reduce the time for temperature equilibrium to less than 3 minutes.

While these deep vacuum systems are optimized for time to sterilization, they are not optimal for the gradual temperature increase required for delicate instruments such as flexible endoscopes. During all phases of the heat up and cool down of the present invention, cycles are optimized not to provide the fastest cycle but are optimized for material compatibility. In one limited example, the exterior of a flexible endoscope component constructed of aluminum can be heated or cooled with lower heat content water or steam relative to interior flexible endoscope components constructed of flexible thermoplastics which can be heated or cooled with higher heat content water or steam. (The heat content of liquid water and of steam is affected by the temperature of the liquid water and the temperature/pressure, and water content or saturation of the steam.) The differential rate of heat transfer can be accomplished by control of the heat content of the steam, water, or both that is flowed in contact with the medical device, and by controlling the flow rate of steam and/or water contacting the medical device. Alternately or in conjunction with the foregoing, differential rate of heat transfer can be accomplished by the temperature and flow rates of warm air. A thermal radiative source of heating can also be used to control heat transfer by the power source of a heat lamp source and distance of the heat lamp source from the endoscope surfaces being heated. The same considerations can be used in the controlled cool down phase of the overall process.

In one embodiment of the present invention, the steam endoscope sterilizer or system 10 can include a thermal sensor capable of a thermal scan of the endoscope or sterilization load. The system can fine-tune the temperature of the delivered solutions to optimize the sterilization time while minimizing the thermal gradient within the device. In this embodiment the system could control the fluids delivered externally and the fluids delivered in the lumens to different temperatures. This system can also optimize the sterilization time based on the thermal characteristics of the load.

As a further embodiment a temperature sensor could be placed in the chamber in view of the thermal sensor, preferably on the cassette 80. The system 10 can read the cassette temperature with both the thermal sensor and the temperature sensor allowing continuous calibration of the thermal image.

Figure 11:
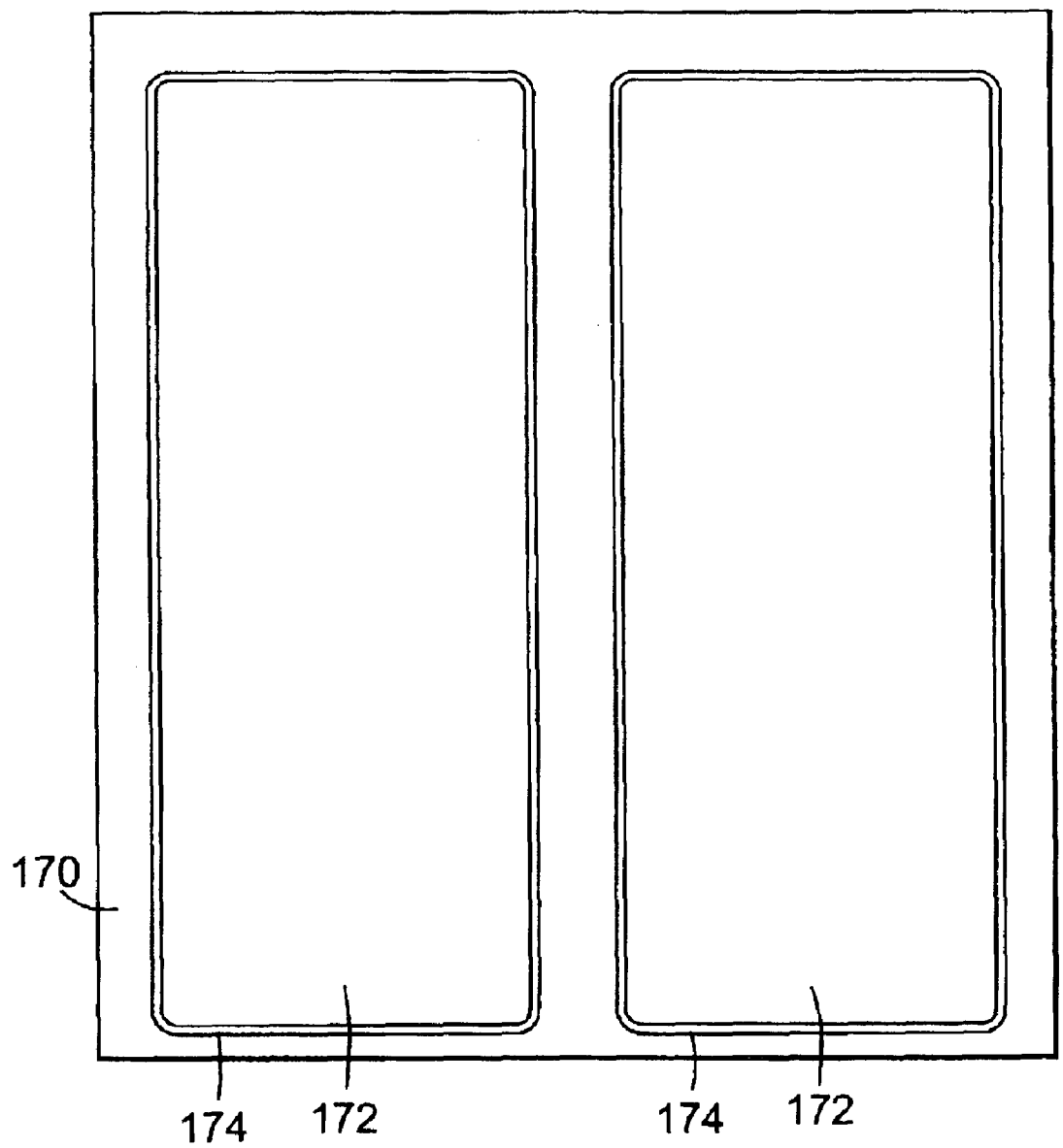
FIG. 11 is a perspective view of a disconnector mechanism useful in conjunction with the embodiments described and shown herein.

In one embodiment of the present invention, the endoscope reprocessing system 10 can be modified with a packaging system for receiving the sterilized endoscope on the endoscope cassette. A sterile packaging system, such as the one described in U.S. Pat. No. 6,234,310, can be used with or modified to fit the present device by attachment to the front plate 170, as shown in FIG. 11 located inside or at the entrance of the reprocessing bay 16 through which one or more plate openings 172 are sized such that a used endoscope and/or endoscope cassette may be inserted into the reprocessing bay 16 and/or such that a reprocessed endoscope and/or cassette may be removed from the bay 16. The front plate 172 can include a lip 174 surrounding each opening 172 that extends outwardly from the system 10, wherein an outer surface of the lip 174 can provide the attachment surface for the sterile bag (not shown). Attachment can be accomplished with a variety of approaches including adhesive on edges of the sterile bag, bands or clamps that hold the bags against the lips 174, and the like. In this embodiment, the removal of the reprocessed endoscope or endoscope cassette can be accomplished in a sterile mode and the package can be sealed, e.g., with adhesive, heat, etc., to maintain sterility within the bag until the moment of use or at least to reduce the likelihood of contamination due to the packaging or via an external contamination source. This modification is intended to enable a user to reprocess and receive a dry sterile endoscope packaged within a dry sterile pouch in contrast to current liquid chemical germicide reprocessing which does not deliver the endoscope in a dry, sterile state.

Figure 12:
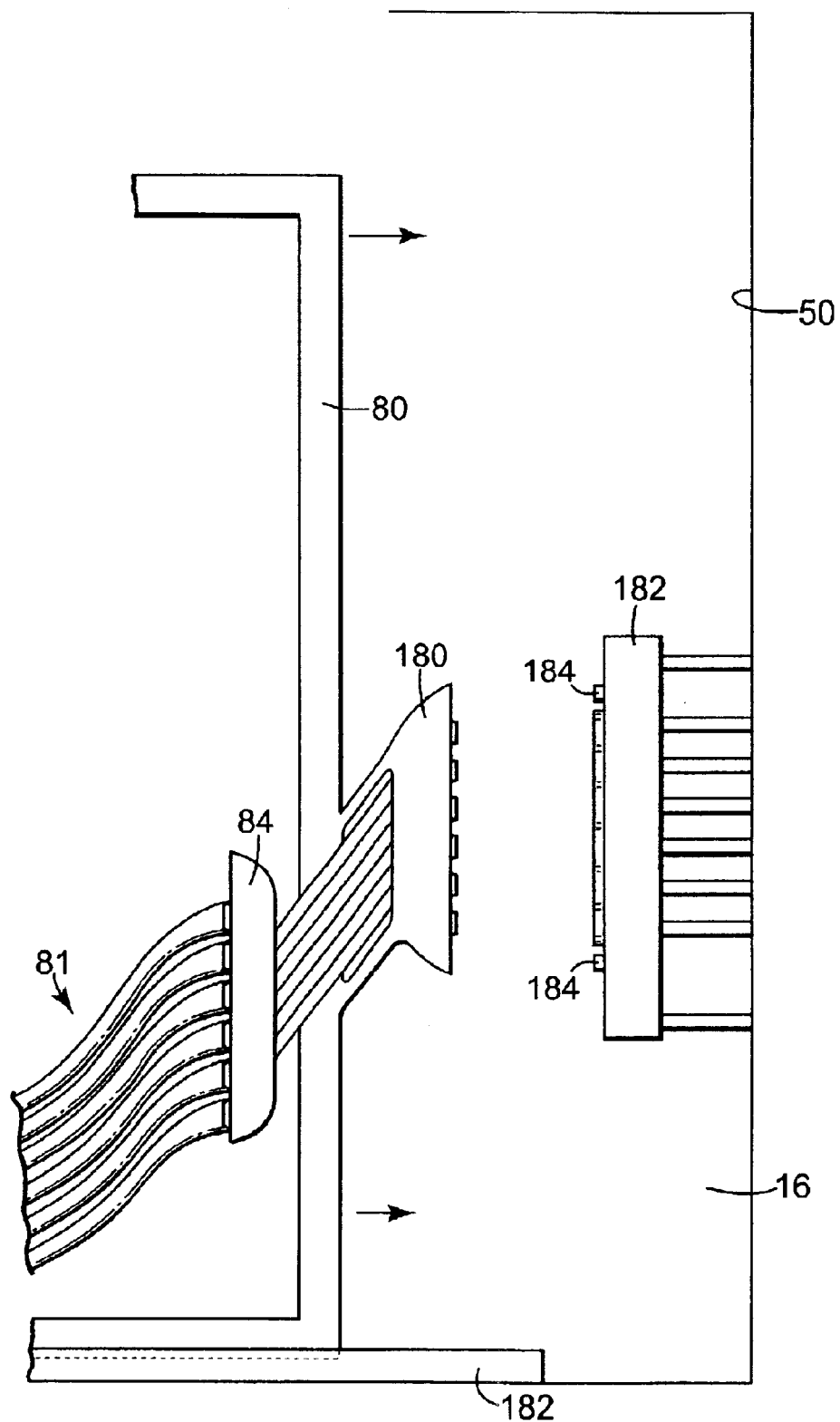
FIG. 12 is a front view of a portion of the embodiments shown and described herein.

FIG. 12 generally illustrates another embodiment or an aspect of the present that can be used in conjunction with other previously described embodiments or aspects. More specifically, the present invention can include first and second aligned fluid connectors 180, 182 that are positioned and configured to bring into fluid communication steam from a steam source (not shown) to the endoscope through the insertion of the endoscope into the system 10. One way this can be accomplished is for first aligned connector 180 to be attached to the leading portion of the cassette 80 (or other frame or structure on which the endoscope is carried) and for second aligned connector 182 to be attached to a structural member of the system 10 at or near the inner portion of the reprocessing chamber 16 such that a connection is made between connectors 180, 182 when the cassette 80 is, for example, slid into the reprocessing bay 16 and guided by guide members positioned on, for example, the lower surface of the reprocessing bay (one of such guide members 184 which is shown). The connection ports of the first and second aligned connectors 180, 182 can be constructed using commercially available fluid connectors. A variety of other approaches or means can be used to make this connection.

Further, this connection can be broken following completion of the reprocessing cycle similarly through a variety approaches and means. For example, disconnect members 184 can be made to extend further outwardly to push first aligned connector 180 away from second aligned connector 182 through the use of one or more air cylinders, electrical motors or actuators, and the like. The extension of the disconnect members 184 can, for example, be carried out by a central processor within the system 10 that has been programmed to do this following the completion of one or more other actions taken by the system 10. The disconnect members 184 can simply be two members each having a circular cross-section, or these members 184 could be a single disconnect member that applies the disconnecting force to, for example, the perimeter of the first aligned connector 180. Alternatively, a similar disconnect mechanism could be placed on the first aligned connector 180 such that the disconnect mechanism pushes against a surface of the second aligned connector 182.

As a further embodiment of the present invention relating to monitoring the sterilization process, a chemical indicator, chemical integrator can be placed within the sterile packaging system such that a visible sign of successful sterilization will remain with the reprocessed endoscope within a sterile bag until the device is ready to use. Additionally, a chemical indicator, chemical integrator or biological indicator can be placed within the sterilization chamber and subsequently removed for reading and recording within the hospital or clinic hospital information system. Examples of monitoring products which are appropriate for this process include 1243 3M™ Comply™ Steam Chemical Integrator, 1255 3M™ Comply™ Steam Indicator Tape and 1291 or 1292 3M™ Attest™ Rapid Readout Biological Indicators. These and other indicators can be used in another embodiment to assess the efficacy of the sterilization process at the most difficult location within an endoscope reprocessing process. The embodiment can comprise a surrogate endoscope lumen which is dimensioned to have the. smallest diameter and the longest path length encountered in the most challenging endoscope. The surrogate endoscope lumen is designed to be attached to one of the steam sterilizer manifolds at the proximal (near) end of the surrogate lumen and connects to a "test piece" at the distal (far) end of the surrogate lumen. The test piece of surrogate lumen contains a biological indicator or a chemical indicator for the steam sterilization process. Alternately, the test piece of the surrogate lumen can contain bioburden test soils or biofilm test soils to test the efficacy of the soil or biofilm removing cleaning segment of the overall steam sterilization process. These test pieces can be removed at the end of the sterilization process and further developed for readout results prior to recording in the hospital or clinic sterilization record keeping system. A variation of this concept would be to insert test pieces or other biological or chemical indicators at one or more locations within lumen of the endoscope.

Presently, flexible endoscopes are constructed of, but not limited to, polyethylene, polyvinyl chloride, Teflon, polyurethane, polypropylene, neoprene, silicone and natural rubber elastomer materials. During a conventional steam sterilization cycle, some of these materials readily soften and distort to no longer be functional during or after the steam exposure. Higher temperature plastics such as polysulfones, polycarbonates and metals are available which provide a higher resistance to the extreme environment of the steam sterilizer, and these materials can be used in the construction of the steam sterilizable cassette, connectors, tubing and flexible packaging associated with the current invention. These materials are referred to, and known to those skilled in the art, as high performance plastics. High performance plastic materials can be used to construct a modified flexible endoscope which survives the extreme heat and moisture environment found in the steam sterilization process. Specific examples of high performance plastics include UDEL brand polysulfones, ULTEM brand polyetherimides and RADEL brand polyether and polyphenylsulfones (Solvay; R-5000, 5100 NT15, 5500, 5800). A specific example of a high performance plastic that is suitable for flexible lumens and tubing is SteamSafe brand tubing, which utilizes a polytetrafluoroethylene (e.g., Teflon brand) innercore that will withstand the extreme temperature fluctuations of most steam service conditions. Blends of engineering plastics are also available with various melting points such that a polymer blend could be used as an indicator that a high performance flexible endoscope is nearing the end of its useful life in the steam sterilization process as an early warning indicator of pending material failure.

The embodiments described herein may be enhanced through the inclusion of heat transfer members as part of the system 10 and/or part of the endoscope (or other device) being reprocessed. One example of this is the inclusion of heat sink members (not shown) in thermal conduction communication with the outer surface of the inner walls of the system 10 to which a cooling fluid may be applied to transfer heat from the interior to the exterior of the system 10. A variety of other heat transfer approaches/devices (actives, passives, or both) can be used to accomplish this transfer.

Also, the endoscope E may be constructed to improve the heat transfer to and from the endoscope E during heat-up and cool-down respectively. For example, the thermal mass of the endoscopes E can be minimized. Similarly, the materials used to construct the endoscopes E can be chosen from more thermally conductive materials, such as a type of stainless steel that is more conductive than another type of stainless steel.

Also, certain portions of the endoscopes E that are exposed to the reprocessing steam can be insulated to a greater degree (in comparison to known endoscopes) from other portions of the endoscopes E to reduce the relevant thermal mass thereby shortening the time in which the portions to be reprocessed rise to a reprocessing temperature during reprocessing and the time in which such portions drop following reprocessing. Such exposed portions can also be made of lesser thermal mass, such as thinner gauge stainless steel than is conventionally used at this time.

The endoscope E can include electronics and electronics enclosure in which electronics is protected. This enclosure can be liquid and gas impermeable to prevent exposure to water, steam, etc. Because the reprocessing apparatus or system 10 can involve the change of pressure within the reprocessing bay 16 and/or lumen of the endoscope, the endoscope E and the system 10 can include means for controlling the pressure within the electronics enclosure to prevent harm thereto. For example, the endoscope can have a gas port into the electronics enclosure that is connectable to a fluid conduit of the system 10 through which air, nitrogen, or another gas can be flowed to maintain or change the pressure with the electronics enclosure as pressure is changed within the reprocessing bay 16 and/or lumen of the endoscope E.

Still other variations of the above-described apparatus, articles, compositions, and methods (including method for using or instructing/recommending use of these aspects) of the present invention are contemplated by the inventors, including other structure, arrangement, composition, and means and steps for providing described functions. It is also clear that the above described embodiments, though possibly most useful for rinsing, cleaning, disinfecting, and/or sterilizing flexible endoscopes, may be and are likely useful on a variety of other medical devices and non-medical devices.

We claim:

1. An apparatus for reprocessing a flexible endoscope, wherein the endoscope has an external surface and a lumen, comprising:
    an enclosure having a reprocessing bay therein for receiving the endoscope;
    a steam source providing steam with at least one controlled heat content in fluid communication with the reprocessing bay;
    a fluid sprayer in fluid communication with the steam source for spraying steam onto the external surface of the endoscope with the steam sprayed onto the external surface of the endoscope having heat content insufficient to damage the endoscope; and
    a fluid conduit in fluid communication with the steam source and configured to allow steam from the steam source to flow through the fluid conduit into the lumen of the endoscope with the steam flowing through the lumen of the endoscope having heat content insufficient to damage the endoscope.

2. The apparatus of claim 1, wherein the lumen comprises a first lumen, wherein the endoscope comprises at least one additional lumen, and wherein the fluid conduit is in fluid communications with the first lumen and additional lumen.

3. The apparatus of claim 2, wherein the fluid conduit comprises polymeric tubing.

4. The apparatus of claim 1, wherein the endoscope comprises a first endoscope, wherein the apparatus is configured to simultaneously reprocessing the first endoscope and a second endoscope.

5. The apparatus of claim 1, wherein the reprocessing bay is configured to withstand pressure above and below on atmosphere.

6. The apparatus of claim 1, further comprising means for changing the pressure within the reprocessing bay.

7. The apparatus of claim 1, further comprising a vacuum pump in fluid communication with the reprocessing bay for changing the pressure within the reprocessing bay.

8. The apparatus of claim 1, further comprising a pressure sensor for sensing the pressure within the reprocessing bay.

9. The apparatus of claim 1, wherein the reprocessing bay is configured to receive a first endoscope and a second endoscope, and wherein the fluid sprayer comprises a first rotating steam member within the reprocessing bay for spraying steam onto the first endoscope and a second rotating steam member within the reprocessing bay for spraying stream onto the second endoscope.

10. The apparatus of claim 9, wherein the fluid sprayer further comprises third and fourth rotating steam members within the reprocessing bay for spraying steam the first and second endoscopes.

11. The apparatus of claim 10, wherein the first, second, third and fourth rotating steam members are configured to spray stem onto the first and second endoscopes in a generally horizontal direction.

12. The apparatus of claim 1, wherein the fluid sprayer comprises a moving sprayer positioned and configured to spray steam onto the endoscope in a generally vertical direction.

13. The apparatus of claim 1, wherein the steam source comprises a first steam generator.

14. The apparatus of claim 1 further comprising means for changing the heat content of the steam sprayed onto or flowed into the endoscope.

15. The apparatus of claim 14, wherein the steam soiree comprises a first steam source, wherein the heat content changing means comprises a second steam source in fluid communication with at least one of the fluid sprayer and the fluid conduit.

16. The apparatus of claim 15, wherein the second steam source is configured to supply steam at a different heat content than the steam supplied by the first steam source.

17. The apparatus of claim 1, further comprising at least one temperature sensor.

18. The apparatus of claim 17, wherein the at least one temperature sensor comprises a temperature sensor positioned to sense steam sprayed onto the endoscope.

19. The apparatus of claim 17, wherein the at least one temperature sensor comprises a temperature sensor positioned to sense steam flowed into the endoscope.

20. The apparatus of claim 17, wherein the at least one temperature sensor comprises a temperature sensor positioned to sense the temperature of a portion of the endoscope.

21. The apparatus of claim 1, wherein the reprocessing bay is configured to receive a first endoscope and a second endoscope, wherein the reprocessing bay includes a first guide and a second guide, wherein the apparatus further comprises a first endoscope support frame on which the first endoscope may be hung and a second endoscope support frame on which the second endoscope may be hung, wherein the first support frame and second support frame are configured to be respectively guided into the reprocessing bay on the first guide and the second guide.

22. The apparatus of claim 21, wherein the apparatus further comprises first and second endoscope conduit connectors respectively for the first and second endoscopes, wherein the first and second endoscope connectors are connectable to openings of lumen of the first and second endoscopes and attachable respectively to the first and second endoscope support frames such that inserting the first or second endoscope support frame having the first or second endoscope hung thereon into the reprocessing bay causes a connection of the first or second endoscope connector to the fluid conduit.

23. The apparatus of claim 1, further comprising a liquid source connected to at least one of the fluid sprayer and the fluid conduit to enable the apparatus to apply a liquid to the endoscope in addition to applying steam.

24. The apparatus of claim 1, wherein the liquid source contains at least one of water, detergent, liquid sterilant, liquid disinfectant, liquid decontaminant, alcohol, and bioflim remover.

25. The apparatus of claim 1, further comprising a chemical source connected to at least one of the fluid sprayer and the fluid conduit to enable the apparatus to apply a chemical gas to the endoscope in addition to applying steam.

26. The apparatus of claim 25, wherein the chemical source contains formaldehyde.

27. The apparatus of claim 1, further comprising a filtered air source connected to at least one of the fluid sprayer and the fluid conduit to enable the apparatus to apply a filtered air to the endoscope in addition to applying steam.

28. The apparatus of claim 1, further comprising: a fluid connector in fluid communication with the steam source and connectable to the endoscope; and means for disconnecting the fluid connector from the endoscope after steam has flow into the endoscope such that the endoscope may be removed from the apparatus.

29. The apparatus of claim 1, further comprising: a fluid connector in fluid communication with the steam source and connectable to the endoscope; arid a disconnector mechanism positioned adjacent the fluid connector for disconnecting the fluid connector from the endoscope after steam has flow into the endoscope such that the endoscope may be removed from the apparatus.

30. The apparatus of claim 1, further comprising a programmable controller that controls actions carried out by the apparatus including at least one of timing of fluid flow onto or Into the endoscope, fluid temperature, fluid type, fluid flow rate, fluid pressure, fluid moisture content.

31. The apparatus of claim 1, further comprising means for affecting the pressure within an electronics enclosure of the endoscope.

32. A method for reprocessing a flexible endoscope, comprising: placing the endoscope into a steam reprocessing bay of a reprocessing apparatus, wherein the endoscope has an exterior surface and lumen; applying steam to the exterior surface of the endoscope; flowing steam through the lumen of the endoscope; and controlling a dimensional change to the endoscope during the reprocessing method.

33. The method of claim 32, wherein the controlling step comprises controlling at least one of expansion or contraction of a material of which the endoscope is made, wherein such material is at least one of a thermoplastic, thermoset, metal glass, and ceramic material.

34. The method of claim 32, wherein the step of providing a flexible cridoscope comprises providing an endoscope comprising a polymeric flexible material, wherein the lumen includes a plurality of lumens.

35. The method of claim 32, wherein at least one of the applying steam and flowing steam steps uses steam having a temperature of between about 121 and about 140 degrees Celsius.

36. The method of claim 32, wherein at least one of the applying stream and flowing steam steps uses steam having a temperature of about 132 degrees Celsius.

37. The method of claim 32, wherein at least one of the applying steam and flowing steam steps uses steam having a temperature of between about 115 and about 126 degrees Celsius.

38. The method of claim 32, wherein at least one of the applying steam and flowing steam steps uses steam having a temperature of about 121 degrees Celsius.

39. The method of claim 32, wherein at least one of the applying steam and flowing steam steps begins using steam having a temperature below 121 degrees Celsius and later continues using a higher temperature steam.

40. The method of claim 32, wherein the steam applied to the exterior and flowed into the lumen is saturated steam.

41. The method of claim 32, wherein the controlling step comprises providing steam for applying steam and flowing steam, wherein the steam providing step comprises changing the temperature of the steam during at least one of the steam applying and steam flowing steps.

42. The method of claim 32, wherein the controlling step comprises controlling the temperature of the steam used in at least one of the applying steam and flowing steam steps.

43. The method of claim 32, wherein the controlling step comprises controlling the temperature of the endoscope In conjunction with at least one of the steam applying and steam flowing steps.

44. The method of claim 32, wherein the controlling step comprises controlling steam pressure in conjunction with at least one of the applying steam and flowing steam steps.

45. The method of claim 32, wherein the controlling step comprises controlling flow rate of the steam in conjunction with at least one of the applying steam and flowing steam steps.

46. The method of claim 32, further comprising: placing the endoscope onto a support frame; attaching an endoscope connector to lumen openings of the endoscope; providing a steam source to supply the steam for the applying steam and flowing steam steps; providing a steam source connector in fluid communication with the steam source and located within the reprocessing bay; and inserting the endoscope such that the endoscope connector connects to the steam source connector.

47. The method of claim 46, further comprising providing at least one guide within the reprocessing chamber that guides the support frame into the reprocessing chamber during the inserting step.

48. The method of claim 32, further comprising applying to the exterior of the endoscope prior to the steam applying step.

49. The method of claim 32, wherein the lumen comprises a plurality of lumens, further comprising flowing a liquid through the lumens of the endoscope prior to the steam flowing step.

50. The method of claim 32, wherein the steps of applying steam and flowing steam and sterilize exterior and interior surfaces of the endoscope.

51. The method of claim 32, further comprising flowing air through at least one lumen of the endoscope following the steam flowing step.

52. The method of claim 32, wherein the steam flowing step comprises a first steam step wherein the steam has a first moisture content into the lumen of the endoscope, wherein the method further comprises a second steam flowing step following the steam flowing step, wherein the steam has a second moisture content into the lumen of the endoscope following the first steam flowing step, wherein the first moisture content is greater than the second moisture content.

53. The method of claim 52, wherein the steam having the second moisture content comprises substantially dry steam to remove condensation from the lumen of the endoscope.

54. The method of claim 32, further comprising at least one of wiping, rinsing, or washing the endoscope before putting the endoscope into the reprocessing bay.

55. The method of claim 32, wherein no wiping, rinsing, or washing of the endoscope occurs before at least one of the steam flowing and steam applying steps.

56. The method of claim 32, further comprising removing the endoscope from the reprocessing bay by a user by reaching into the reprocessing bay through a sterile bag such that the endoscope does not contact a non-sterile bag during the removing step.

57. The method of claim 56, further comprising attaching the sterile bag to the reprocessing apparatus prior to reaching into the reprocessing bay.

58. The method of claim 32, wherein placing the endoscope into the steam reprocessing bay causes a first connector in fluid communication with a lumen of the endoscope to connect to a second connector in communication with the reprocessing apparatus such that steam from the reprocessing apparatus may flow into the lumen.

59. The method of claim 32, further comprising controlling the rate at which the endoscope contracts when cooled to reduce damage to a material of which the endoscope is made.

60. The method of claim 59, wherein the controlling of the cooling rate comprises at least one of controlling the temperature, moisture content, and flow rate of at least one of water, alcohol, other liquid, steam, air, and other gas flowed into or onto the endoscope.

61. The method of claim 32, further comprising flowing gas between an endoscope enclosure that encloses electronics of the endoscope and a gas source of the reprocessing apparatus to change pressure within the electronics enclosure.

62. An endoscope assembly for use with a endoscope reprocessing apparatus, comprising:
   an endoscope having lumen therein;
   a frame on which the endoscope may be positioned during reprocessing within a reprocessing apparatus, wherein the flame includes an assembly connector connectable to the lumen such that reprocessing fluid from the reprocessing can flow into the lumen, wherein a reprocessor connector is positioned and configured to connect to a reprocessing connector of the reprocessing apparatus due to insertion of the frame into the reprocessing apparatus.

63. The endoscope assembly of claim 62, wherein the frame comprises means for holding the endoscope that is integral with the assembly connector.

64. The endoscope assembly of claim 62, further comprising a fluid set connectable to and between the endoscope and the assembly connector such that reprocessing fluid from the reprocessing apparatus can flow through the assembly connector and the fluid set and into the lumen.

65. The endoscope assembly of claim 62, wherein the endoscope includes a lumen entrance port in which reprocessing fluid can enter the lumen and a lumen exit port through which reprocessing fluid can exit the lumen.

66. The endoscope assembly of claim 62, wherein the endoscope has electronics within an electronic enclosure, and wherein the endoscope enclosure has a gas port for receiving a gas from a gas source to affect the pressure within the electronics enclosure.

67. A method for reprocessing the endoscope following an endoscopic procedure, comprising placing the endoscope into a steam reprocessing bay of a reprocessing apparatus, wherein the endoscope has an exterior surface and lumen; applying steam to the exterior surface of the endoscope; flowing flow of steam through the lumen of the endoscope; and controlling the temperature the endoscope during the reprocessing method.

68. The method of claim 67, wherein the endoscope was used in an endoscopic procedure prior to the placing step.

* * * * *

UNITED STATES PATENT AND TRADEMARK OFFICE
CERTIFICATE OF CORRECTION

| | |
|---|---|
| PATENT NO. | : 6,884,392 B2 |
| APPLICATION NO. | : 10/292747 |
| DATED | : April 26, 2005 |
| INVENTOR(S) | : Malkin et al. |

It is certified that error appears in the above-identified patent and that said Letters Patent is hereby corrected as shown below:

Column 3, line 53, delete "temperature the" and substitute --temperature of the-- therefor.
Column 8, line 48, delete "Alteniatively..." and substitute --Alternatively-- therefor.
Column 8, line 54, delete "...tat..." and substitute --that-- therefor.
Column 8, line 59, delete "be communication" and substitute --be in communication-- therefor.
Column 8, line 66, delete "...anpther..." and substitute --another-- therefor.
Column 9, line 2, delete "...die endoscope..." and substitute --the endoscope-- therefor.
Column 12, line 29, delete "in the art;" and substitute --in the art-- therefor.
Column 12, line 37, delete "for purpose" and substitute --for the purpose-- therefor.
Column 13, line 32, delete "...repeated,..." and substitute --repeated-- therefor.
Column 14, line 58, delete "...immediately-preceding..." and substitute --immediately preceding-- therefor.
Column 21, line 17, delete "of surrogate" and substitute --of the surrogate-- therefor.
Column 21, line 28, delete "within lumen" and substitute --within the lumen-- therefor.
Column 23, line 12, delete "...below on..." and substitute --below one-- therefor
Column 23, line 27, delete "spraying stream" and substitute --spraying steam-- therefor.
Column 23, line 34, delete "...spray stem..." and substitute --spray steam-- therefor.
Column 23, line 45, delete "...steam soiree..." and substitute --steam source-- therefor.
Column 25, line 4, delete "...flexible cridoscope..." and substitute --flexible endoscope-- therefor.
Column 26, line 17, delete "...putting..." and substitute --placing-- therefor.
Column 26, line 23, delete "...non-sterile bag..." and substitute --non-sterile surface-- therefor.
Column 26, line 50, delete "...having lumen..." and substitute --having a lumen-- therefor.

UNITED STATES PATENT AND TRADEMARK OFFICE
CERTIFICATE OF CORRECTION

PATENT NO.       : 6,884,392 B2
APPLICATION NO.  : 10/292747
DATED            : April 26, 2005
INVENTOR(S)      : Malkin et al.

It is certified that error appears in the above-identified patent and that said Letters Patent is hereby corrected as shown below:

Column 27, line 2, delete "...port in which..." and substitute --port into which-- therefor.
Column 27, line 6, delete "...electronic..." and substitute --electronics-- therefor.

Signed and Sealed this

Fifteenth Day of August, 2006

JON W. DUDAS
*Director of the United States Patent and Trademark Office*